US006362479B1

United States Patent
Andreaco et al.

(12) United States Patent
(10) Patent No.: US 6,362,479 B1
(45) Date of Patent: Mar. 26, 2002

(54) SCINTILLATION DETECTOR ARRAY FOR ENCODING THE ENERGY, POSITION, AND TIME COORDINATES OF GAMMA RAY INTERACTIONS

(75) Inventors: Mark S. Andreaco, Knoxville; Charles W. Williams, Powell; Ronald Nutt; Michael E. Casey, both of Knoxville, all of TN (US)

(73) Assignee: CTI PET Systems, Inc., Knoxville, TN (US)

(*) Notice: Subject to any disclaimer, the term of this patent is extended or adjusted under 35 U.S.C. 154(b) by 0 days.

(21) Appl. No.: 09/272,228

(22) Filed: Mar. 18, 1999

Related U.S. Application Data

(60) Provisional application No. 60/079,279, filed on Mar. 25, 1998.

(51) Int. Cl.[7] .................................................. G01T 1/20
(52) U.S. Cl. .................. 250/366; 250/367; 250/363.01; 250/363.03; 250/363.1
(58) Field of Search ................................. 250/366, 367, 250/363.01, 363.03, 363.1

(56) References Cited

U.S. PATENT DOCUMENTS

| | | |
|---|---|---|
| 2,910,592 A | 10/1959 | Armistead |
| 3,432,660 A | 3/1969 | Anger |
| 3,851,177 A | 11/1974 | Van Dijk et al. |
| 3,899,675 A | 8/1975 | Floyd |
| 3,919,556 A | 11/1975 | Berninger |
| 3,955,088 A | 5/1976 | Muehllehner et al. |
| 4,037,105 A | 7/1977 | Laurer |
| 4,075,483 A | 2/1978 | Tancrell et al. |
| 4,095,107 A | 6/1978 | Genna et al. |
| 4,124,804 A | 11/1978 | Mirell |
| 4,323,778 A | 4/1982 | Wykes et al. |
| 4,398,092 A | 8/1983 | Carlson |

(List continued on next page.)

OTHER PUBLICATIONS

C.A. Burnham, et al., MGH Cylindrical PET Detector Characteristics, pp. 1644–1647, Feb. 1992.

J.C. Moyers: "A High Performance Detector Electronics System for Positron Emission Tomography", Master Thesis, University of Tennessee, Knoxville, TN 1990.

R.A. DeKemp, et al.: "Attenuation Correction in PET Using Single Photon Transmission Measurement", Med. Phys., vol. 21, 771–8, 1994.

(List continued on next page.)

Primary Examiner—Constantine Hannaher
Assistant Examiner—Andrew Israel
(74) Attorney, Agent, or Firm—Pitts & Brittian, P.C.

(57) ABSTRACT

A scintillation detector which includes a plurality of discrete scintillators composed of one or more scintillator materials. The discrete scintillators interact with incident radiation to produce a quantifiable number of photons with characteristic emission wavelength and decay time. A light guide is operatively associated with the scintillation crystals and may be either active or non-active and segmented or non-segmented depending upon the embodiment of the design. Photodetectors are provided to sense and quantify the scintillation light emissions. The process and system embodying various features of the present invention can be utilized in various applications such as SPECT, PET imaging and simultaneous PET systems. In accordance with the present invention, the detector array of the present invention incorporates either a single scintillator layer of discrete scintillators or discrete scintillators composed of two stacked different layers that can be the same scintillator material or of two different scintillator materials. In either case the different layers are composed of materials that have distinctly different decay times. The variants in these figures are the types of optical detectors which are used, i.e. photomultipliers and/or photodiodes, whether or not a segmented optical light guide is used, and whether the light guide is active or non-active. If a segmented optical light guide is used then the variant is whether the configuration is inverted or non-inverted.

72 Claims, 33 Drawing Sheets

U.S. PATENT DOCUMENTS

| | | | |
|---|---|---|---|
| 4,531,058 A | | 7/1985 | Burnham et al. |
| 4,667,299 A | | 5/1987 | Dunn |
| 4,675,526 A | | 6/1987 | Rogers et al. |
| 4,677,299 A | | 6/1987 | Wong |
| 4,687,683 A | | 8/1987 | Ishii et al. |
| 4,743,764 A | | 5/1988 | Casey et al. |
| 4,749,863 A | | 6/1988 | Casey et al. |
| 4,750,972 A | | 6/1988 | Casey et al. |
| 4,837,439 A | | 6/1989 | Genna et al. |
| 4,843,245 A | | 6/1989 | Lecomte |
| 4,891,520 A | | 1/1990 | Ishibashi et al. |
| 5,107,121 A | | 4/1992 | Lim et al. |
| 5,122,667 A | | 6/1992 | Thompson |
| 5,210,420 A | | 5/1993 | Hartz et al. |
| 5,264,154 A | | 11/1993 | Akiyama et al. |
| 5,319,204 A | | 6/1994 | Wong |
| 5,332,906 A | | 7/1994 | Lauf et al. |
| 5,338,936 A | | 8/1994 | Gullberg et al. |
| 5,349,191 A | | 9/1994 | Rogers |
| 5,430,297 A | | 7/1995 | Hawman |
| 5,434,416 A | | 7/1995 | Motomura et al. |
| 5,453,623 A | | 9/1995 | Wong et al. |
| 5,471,061 A | | 11/1995 | Moyers et al. |
| 5,479,021 A | | 12/1995 | Morgan et al. |
| 5,608,221 A | | 3/1997 | Bertelsen et al. |
| 5,650,625 A | | 7/1997 | Stoub |
| 5,750,991 A | | 5/1998 | Moyers et al. |
| 6,087,663 A | * | 7/2000 | Moisan et al. ............... 250/367 |

OTHER PUBLICATIONS

S.R. Cherry, et al.: "3D–PET Using a Conventional Tomograph Without Septa", Jl. C.A.T., 15(4)655–668.

J.S. Karp, et al.: "Singles Transmission in Volume–Imaging PET With a 137 Cs Source", Phys. Med. Biol. vol. 40, 929–944, 1995.

S.K. Yu, et al.: Single–Photon Transmission Measurements in Position Tomography Using 137 Cs:, Phys. Med. Biol. vol. 40, 1255–1266, 1995.

S.R. Cherry, et al.: "Optical Fiber Readout of Scinillator Arrays Using a Multi–Channel PMT: A High Resolution PET Detector for Animal Imaging", IEEE Transactions on Nuclear Science, vol. 43, No. 3, 1932–1937, Jun. 1996.

J.A. McIntyre, et al.: "Construction of a Position Emission Tomograph with 2.4 mm Detectors", IEEE Transactions on Nuclear Science, vol. 33, No. 1, 425–427, Feb., 1986.

M. Dahlbom, et al.—Performance of a YSO/LSO Phoswich Detector for use in a PET/SPECT System IEEE Transactions on Nuclear Science, vol. 44, No. 3, Jun., 1997, pp. 1114–1119.

G.B. Loutts, et al.—Czochralski growth and characterization of (Lu 1–x Gd x) 2 SiO 5 single crystals for scintillators Journal of Crystal Growth 174 (1997) pp. 331–336.

P. Tan, et al.—A Scanning Line Source for Simultaneous Emission and Transmission Measurements in SPECT The Journal of Nuclear Medicine, vol. 34, No. 10, Oct. 1993.

D.L. Bailey, et al.—Improved SPECT Using Simultaneous Emission and Transmission Tomography The Journal of Nuclear Medicine, vol. 28, No. 5, May 1987.

H. M. Hudson and R.S. Larkin—Accelerated Image Reconstruction Using Ordered Subsets of Projection Data IEEE Transactions on Medical Imaging, vol. 13, No. 4, Dec. 1994.

L.T. Chang—A Method for Attenuation Correction in Radionuclide Computed Tomography IEEE Transactions on Nuclear Science, vol. NS–25, No. 1, Feb. 1978.

E.F. Hollinger, et al.—Using Fast Sequential Asymmetric Fanbeam Transmission CT for Attenuation Correction of Cardiac SPECT Imaging—The Journal of Nuclear Medicine, vol. 39, No. 8, Aug. 1998.

K. Lange, et al.—A Theoretical Study of Some Maximum Likelihood Algorithms for Emission and Transmission Tomography—IEEE Transactions on Medical Imaging, vol. MI–6, No. 2, Jun. 1987.

G.T. Gullberg, et al.—An Attenuation Projector–Backprojector for Iterative SPECT Reconstruction Phys. Med. Biol., 1985, vol. 30, No. 8, 799–816.

K. Lange and R. Carson—EM Reconstruction Algorithms for Emission and Transmission Tomography Journal of Computer Assisted Tomography 8(2): 306–313, Apr. 1984.

* cited by examiner

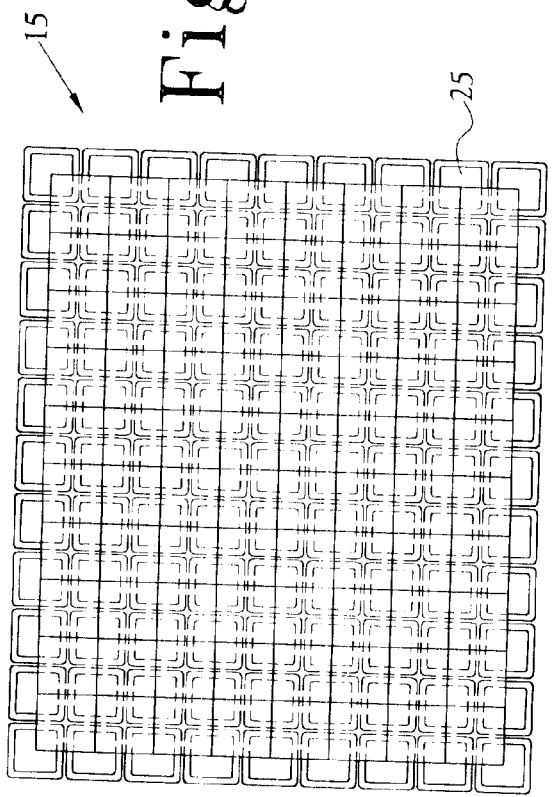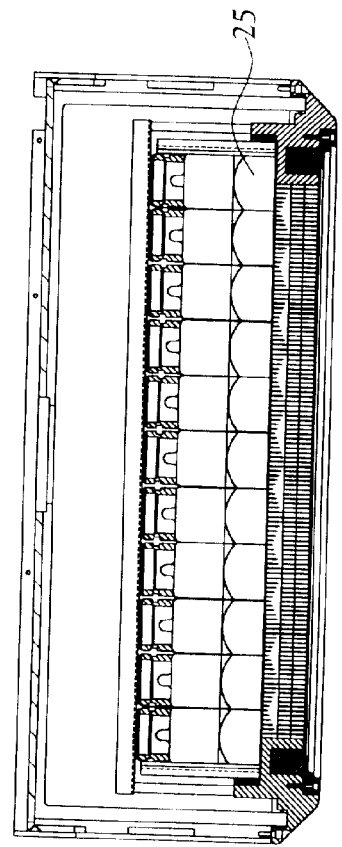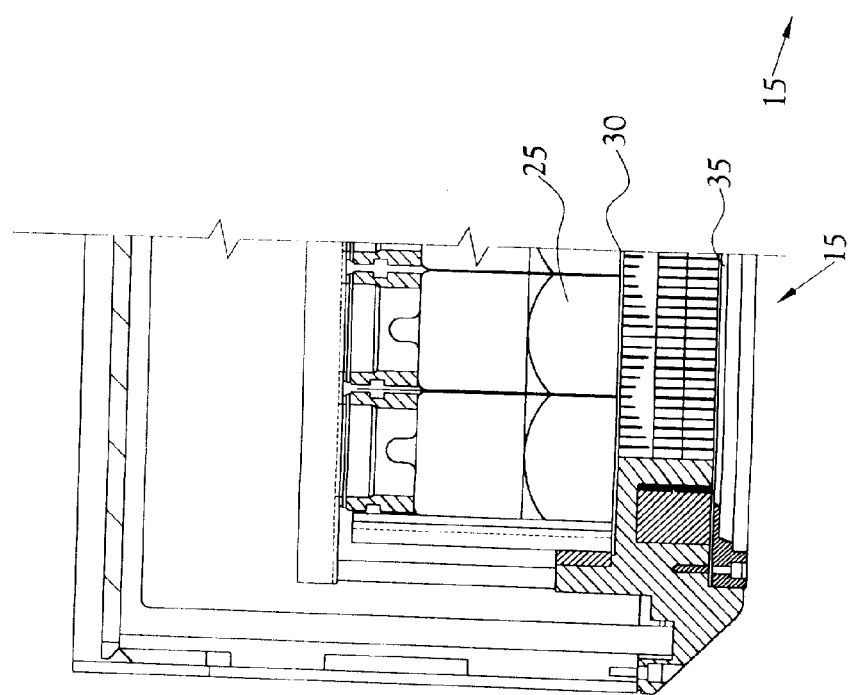

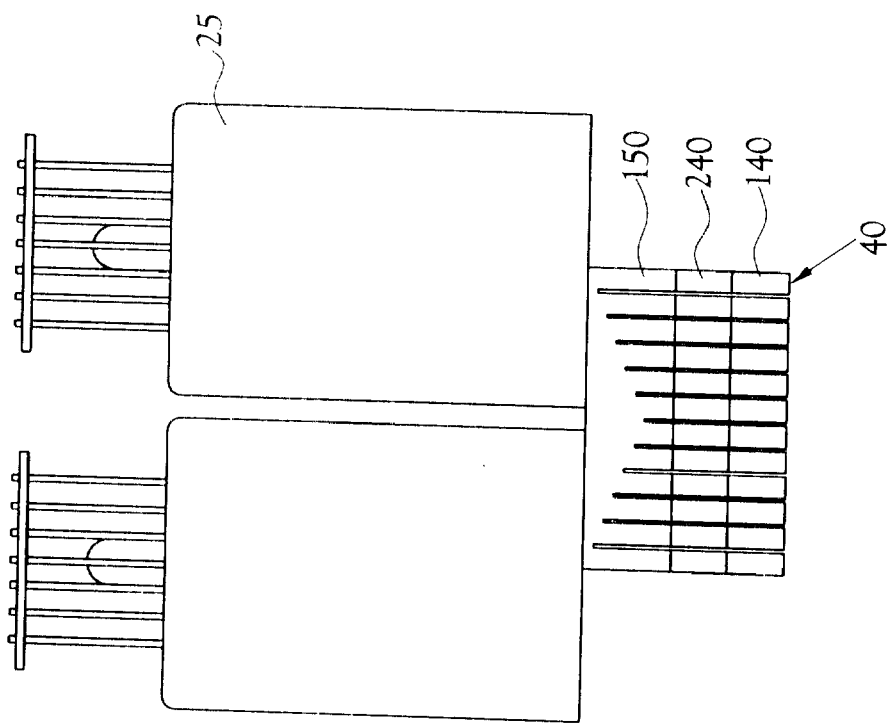
Fig.3g₁
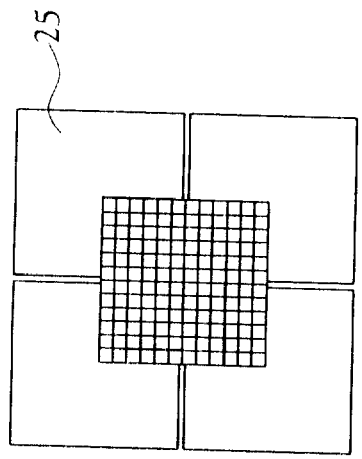
Fig.3g₂

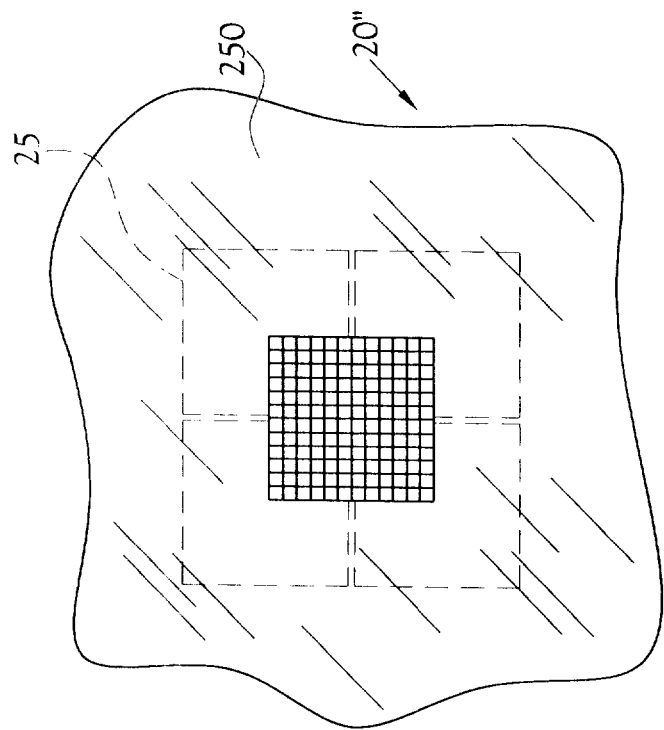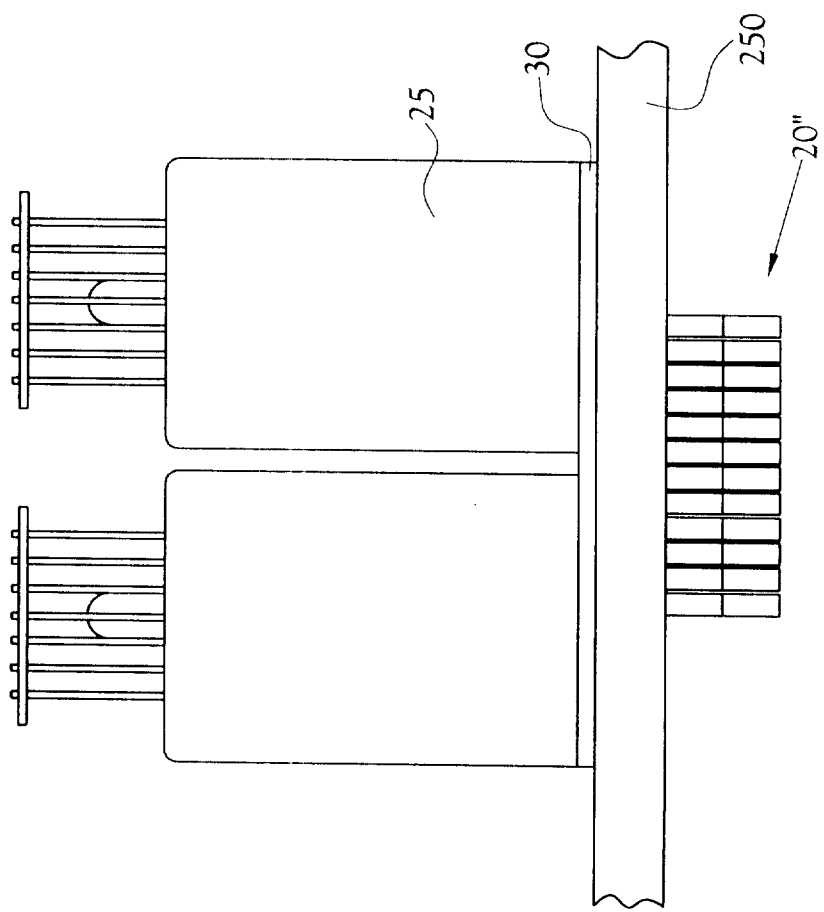
Fig. 8

PET/SPECT Coincidence Timing

SCINTILLATION DETECTOR ARRAY FOR ENCODING THE ENERGY, POSITION, AND TIME COORDINATES OF GAMMA RAY INTERACTIONS

This application claims the benefit of U.S. Provisional Application No. 60/079,279, filed Mar. 25, 1998.

TECHNICAL FIELD

The present invention relates to an apparatus capable of determining the energy, position and time coordinates of light emission induced by interactions of gamma-rays in a planar array of discrete scintillator detectors having either a segmented or non-segmented light guide. The features of the present invention find particular application in the field of medical imaging whereby a single device can be used for Single Photon Imaging which includes traditional Gamma Cameras, Planar Imaging, Single Photon Emission Computed Tomography (SPECT) with or without Coincidence Photon Imaging and Positron Emission Tomography (PET). When operated in the SPECT mode, the present invention is comparable to existing high resolution SPECT systems. When operated in the PET mode, the present invention is an improvement over existing PET systems in that the device may be operated either in Pulse Height Discrimination mode or in Pulse Shape Discrimination mode thereby enabling depth of interaction encoding resulting in improved spatial resolution. Emission Computed Tomography (ECT) systems provide a means for sensing, and quantitatively measuring biochemical and/or physiological changes in the human body or other living organism. However, the use of the invention is not limited to such application.

BACKGROUND ART

Devices for detecting the distribution of gamma rays transmitted or emitted through objects to study the compositions or functions of the objects are well known to the art, e.g. the techniques referred to as Emission Computed Tomography can be divided into two specific classes; Single Photon Emission Computed Tomography (SPECT) uses radiotracers which emit gamma rays but do not emit positrons and Positron Emission Tomography (PET) which uses radiotracers that emit positrons. Therefore, the fundamental physical difference between the two techniques is that PET uses annihilation coincidence detection. The PET technique can determine, in-vivo, biochemical functions, on the injection of biochemical analog radiotracer molecules that emit positrons in a living body. The positrons annihilate with surrounding electrons in the subject body to produce a pair of gamma-rays, each having 511 keV of photon energy; traveling in nearly opposite directions. The detection of a pair of annihilation gamma-rays by two opposed detectors allows for the determination of the location and direction in space of a trajectory line defined by the opposite trajectories of the gamma-rays. Tomographic reconstruction is then used to superpose the numerous trajectory lines obtained by surveying the subject with an array of detectors to image the distribution of radiotracer molecules in the living body.

Emission Computed Tomography systems employ a variety of geometric configurations for the gamma-ray detectors. The choice of configuration is typically dictated by the manufacturer's desired system performance and cost. The detector design must be capable of providing accurate estimates of gamma-ray energy, position coordinates, and in addition in the case of PET, coincidence time interval to reconstruct an image of the distribution of the radiotracer for in vivo studies. An example of such a device is disclosed in U.S. Pat. No. 4,750,972 to Casey et al., the disclosure of which is incorporated herein by reference and relied upon.

The position encoder and detector system disclosed by Casey et. al., is a two dimensional photon counting position encoder detector system, i.e., the array of scintillation crystals provides only the transverse coordinates of the photon interaction; the longitudinal photon interaction position of the excited scintillation crystal is undetermined. Photons impinging upon such detector systems at angles other than normal may traverse the path of several scintillation crystals resulting in uncertainty of their trajectory lines thereby degrading the image resolution due to parallax error.

A detector system capable of providing both the transverse and longitudinal position of photon interactions in scintillation crystals was disclosed in U.S. Pat. No. 4,843,245 by Lecomte. The approach involves the use of two scintillation crystals of different decay times which are stacked one upon the other. The position of photon interaction is determined by the Pulse Shape Discrimination technique. This method though capable of providing the transverse and longitudinal position coordinates of photon interactions in scintillation crystal detector systems will result in reduced system efficiency if the overall scintillator depth is constant for two different scintillator materials. If the scintillators are increased in length to compensate for the efficiency loss then the system resolution will be degraded.

Another approach to determine the transverse and longitudinal positions of photon interactions in scintillation crystal detector systems was disclosed in U.S. Pat. No. 5,122,667 by Thompson. The approach differs from that of Lecomte in that a single scintillator is used, further the method does not depend on decay time differences. The method employs the use of a scintillation light absorbing band located at the median interaction coordinate for a specific energy along the longitudinal axis of the scintillation crystal. The net effect is to divide the scintillation crystal into two regions whereby the photon is equally likely to interact. Pulse Height Discrimination is used to determine which of the two regions of the scintillator the photon interacted. This approach has the undesired effect of reducing the total collected scintillation light and of causing the Compton continuum of the high light yield scintillator to overlap the photopeak region of the low light yield scintillator. The result is inherent uncertainty in the contribution of scatter to the full energy photopeak.

In U.S. Pat. No. 5,349,191 Rogers discloses a method for determining the transverse and longitudinal position coordinates for interactions in scintillation crystal arrays which depends on the continuous variation of the total collected light with the longitudinal photon interaction coordinate of the light emission. The continuous variation in collected light requires a complex calibration of each detector as a function of longitudinal photon interaction coordinate from a collimated beam of photons directed at known positions along the length of the scintillator. This calibration method is difficult to implement for large arrays of scintillators.

In U.S. Provisional Application Ser. No. 60/037,519, filed on Feb. 10, 1997, and U.S. Provisional Application Ser. No. 60/042,002, filed on Apr. 16,1997, Moisan and Andreaco et. al. disclosed a device capable of determining the transverse and longitudinal coordinates of light emission induced by the interaction of photons in an array of photon detectors having a plurality of scintillation light guides. The device uses two or more layers of stacked scintillators all composed of the same scintillator material. Pulse Height Discrimination is used to determine which scintillator layer the photon interaction occurs. The device requires a difference in the light output from the two stacked scintillator layers of at least a factor of 1.5 times for the pulse height discrimination technique to be practicable. The approach has the undesired effect of causing the Compton continuum of the high light yield scintillator (which is nearest to the subject under study) to overlap the photopeak region of the low light yield scintillator. The result is inherent uncertainty in the contribution of scatter to the full energy photopeak.

The detector systems described in the above stated U.S. Patents when applied to medical imaging are specific to usage in PET. The predominant scintillator material is Bismuth Germanate (BGO), though other materials have been proposed or used (see Table 1). The SPECT detector systems are different in that Thallium doped Sodium-Iodide (NaI(Tl)) is used exclusively as the scintillator material. Further these systems use large continuous slabs of NaI(Tl) optically coupled to a continuous light guide. Anger logic is used for scintillation event localization. The exception to continuous NaI(Tl) slab detector systems for SPECT imaging was disclosed by Govaert in U.S. Pat. No. 4,267,452. This detector system is unique as a SPECT detector in that it is segmented. The segmentation of the NaI(Tl) is similar to PET block detector designs which use an active light guide. (For clarification detector light guides are of two general types: non-active light guides are composed of optical materials other than the scintillator; active light guides are composed of scintillator materials). The detector system disclosed by Govaert does not result in discrete scintillator elements whereby each element is a separate detector. Instead the segmentation process results in a block of NaI(Tl) that is subdivided into elements that share a common light guide of active scintillator material, i.e. the NaI(Tl) is not cut all the way through.

Other patents known to the inventors include the following:

| U.S. Pat. No. | Issued to | Date of Issuance |
| --- | --- | --- |
| U.S. Pat. No. 2,910,592 | Armistead | Oct. 27, 1959 |
| U.S. Pat. No. 3,851,177 | Van Dijk, et al | Nov. 16, 1974 |
| U.S. Pat. No. 3,899,675 | Floyd | Aug. 12, 1975 |
| U.S. Pat. No. 3,919,556 | Berninger | Nov. 11, 1975 |
| U.S. Pat. No. 3,955,088 | Meuhilehner, et al | May 4, 1976 |
| U.S. Pat. No. 4,037,105 | Laurer | July 19, 1977 |
| U.S. Pat. No. 4,075,483 | Tancrell et al | Feb. 21, 1978 |
| U.S. Pat. No. 4,095,107 | Genna, et al | June 13, 1978 |
| U.S. Pat. No. 4,124,804 | Mirell | Nov. 7, 1978 |
| U.S. Pat. No. 4,323,778 | Wykes, et al | Apr. 6, 1982 |
| U.S. Pat. No. 4,398,092 | Carlson | Aug. 9, 1983 |
| U.S. Pat. No. 4,675,526 | Rogers et al | June 23, 1987 |
| U.S. Pat. No. 4,677,299 | Wong | June 30, 1987 |

The unique differences in SPECT and PET imaging modalities have resulted in detector designs which are suitable for their intended use in either SPECT or PET, but not both. However, the use of Fluorodeoxyglucose (FDG) with SPECT imaging systems has resulted in the application of SPECT detector designs in PET imaging. One problem in the application of SPECT detector designs in PET is that relatively thin scintillation crystals are preferred in Anger cameras to provide better intrinsic resolution and image detail. This results in poor detection efficiency in PET since the effective-Z and density of NaI(Tl) provides lower stopping power at 511 keV relative to PET scintillators (see Table 1). The efficiency of SPECT detector systems is further reduced by the use of absorptive collimation. The continuous slab of NaI(Tl) precludes the elimination of absorptive collimation.

SPECT detector system designs which are intended to bridge both SPECT and PET imaging modalities are known as hybrid devices. These systems have increased the NaI(Tl) scintillator thickness for higher efficiency and have added coincidence detection circuitry and attenuation corrections. Despite these changes the continuous slab of NaI(Tl) scintillator detector designs are inferior to PET specific detector designs in terms of system performance.

The hybrid SPECT detector designs have compromised their SPECT performance while providing inferior PET performance. A need has arisen for a hybrid PET/SPECT detector system which provides state of the art SPECT and PET system performance which does not suffer from the heretofore stated disadvantages.

Accordingly, it is an object of the present invention to provide a detector system design which does not suffer from the heretofore stated disadvantages.

Another object of this invention is to provide a detector system design for the detection of radioactive events inclusive of single photon emitters and positron emitters.

A further object of this invention is to provide a detector system for imaging radioactive event distributions.

A still further object of this invention is to provide a detector system for planar and tomographic imaging.

It is yet another object of the present invention to provide a detector system for use in both SPECT and PET imaging.

A further object of the present invention is to provide a detector system with depth of interaction encoding.

It is another object of the present invention to provide a detector system with active shielding against background and scatter radiation.

A further object of the present invention is to effectively eliminate scintillator self-radiation by the use of pulse shape discrimination.

A still further object of the present invention is to provide a detector with time-of-flight encoding in one or more embodiments of the design.

Other objects and advantages of the present invention will become more apparent upon review of the detailed description and associated drawings of the scintillator detector array for encoding the energy, position and time coordinates of gamma-ray interactions.

DISCLOSURE OF THE INVENTION

In accordance with the various features of this invention, a scintillation detector is provided which includes a plurality of discrete scintillators composed of one or more scintillator materials. The discrete scintillators interact with incident radiation to produce a quantifiable number of photons with characteristic emission wavelength and decay time. A light guide is operatively associated with the scintillation crystals and may be either active or non-active and segmented or non-segmented depending upon the embodiment of the design. Photodetectors are provided to sense and quantify the scintillation light emissions. The process and system embodying various features of the present invention can be utilized in various applications such as SPECT and PET imaging systems. In accordance with the present invention, the detector array of the present invention incorporates either a single layer of discrete scintillators or discrete scintillators composed of two stacked different layers that can be the same scintillator material or of two different scintillator materials. In either case the different layers are composed of materials that have distinctly different decay times. The variants in these figures are the types of optical detectors which are used, i.e. photomultipliers and/or photodiodes, whether or not a segmented optical light guide is used, and whether the light guide is active or non-active. If a segmented optical light guide is used then the variant is whether the configuration is inverted or non-inverted.

BRIEF DESCRIPTION OF THE DRAWINGS

The above mentioned features of the invention will become more apparent from consideration of the following description when read together with the accompanying drawings, in which:

FIG. 2 is comprised of FIG. 2a through and inclusive of FIG. 2e. These figures present various views of the detector head of the system illustrated in FIG. 1 and the detector blocks as mounted in the detector head. FIG. 2a depicts an 8×10 array of detector blocks optically coupled to a 9×11 array of photomultiplier tubes. FIGS. 2b and 2c illustrate cross-sectional views of the detector head in which the array of detector blocks are optically coupled to an array of photomultiplier tubes.

FIG. 3 is comprised of FIG. 3(a) through and inclusive of FIG. 3(1). These figures present a perspective view of the types of detector blocks which could be incorporated in the detector head illustrated in FIG. 2. The common feature in these figures is the embodiment of the design incorporating discrete scintillators composed of two stacked different scintillator materials of different decay times. The variants in these figures are the types of optical detectors which are used, i.e. photomultipliers and/or photodiodes. The other variant is whether or not a segmented optical light guide is used. If a segmented optical light guide is used then one variant is whether the configuration is inverted or non-inverted. Another variant is whether the light guide is active or non-active.

FIG. 3(g) is a perspective view of one detector block from the detector head illustrated in FIG. 2 for another embodiment of the design incorporating discrete scintillators composed of two stacked different scintillator materials of different decay times optically coupled to a non-active segmented non-inverted light guide. The light guide is optically coupled to PMTs. The PMTs are the optical detectors.

FIG. 3(l) is a perspective view of an alternative detector block applicable to any of the embodiments discussed herein showing that the perimetric dimensions of a single detector block, which in one embodiment is defined by a 12×12 discrete element array can be coextensive with the perimetric dimension of a 2×2 array of four optical detectors. The segmented light guide can be inverted or non-inverted, active or non-active.

FIG. 4 and 4a illustrate a side elevation and plan, respectively, of one detector block from the detector head illustrated in FIG. 2 for another embodiment of the design incorporating discrete scintillators composed of two stacked different scintillator materials of different decay times optically coupled to a non-active non-segmented light guide. The light guide is optically coupled to the PMTs. The PMTs are the optical detectors.

FIGS. 6 and 6a illustrate side elevation and plan views, respectively, of one detector block from the detector head illustrated in FIG. 2 for another embodiment of the design incorporating discrete scintillators composed of a single scintillator material optically coupled to a non-active non-segmented light guide. The light guide is optically coupled to the PMTs. The PMTs are the optical detectors.

FIG. 8 is a perspective view of one detector block from the detector head illustrated in FIG. 2 for another embodiment of the design incorporating discrete scintillators composed of a single scintillator material of two different decay times optically coupled to a non-active non-segmented light guide. The light guide is optically coupled to the PMTs. The PMTs are the optical detectors.

FIG. 13 illustrates the effectiveness of the detector design and the pulse shape separation technique.

BEST MODE FOR CARRYING OUT THE INVENTION

Figure 1:
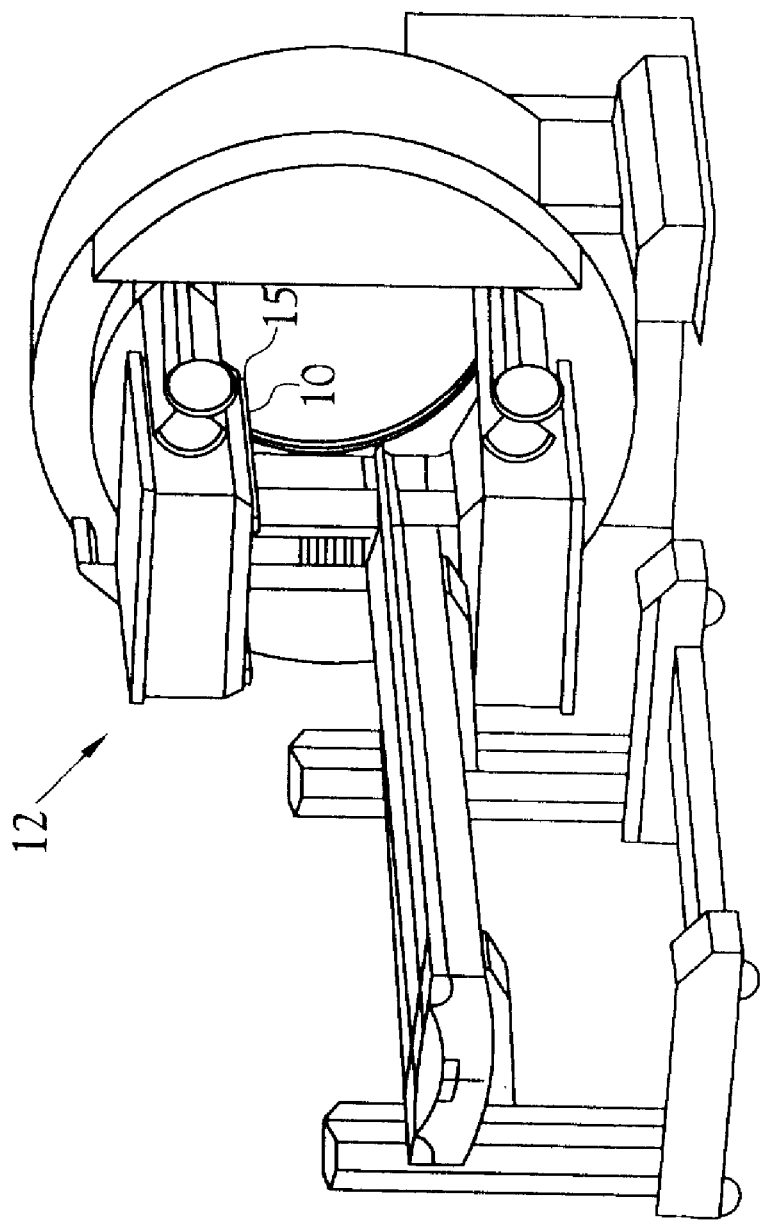
FIG. 1 is a perspective view of a medical imaging scanner embodying scintillation detector arrays for encoding the energy, position and time coordinates of gamma-ray interactions.
Figure 2E:
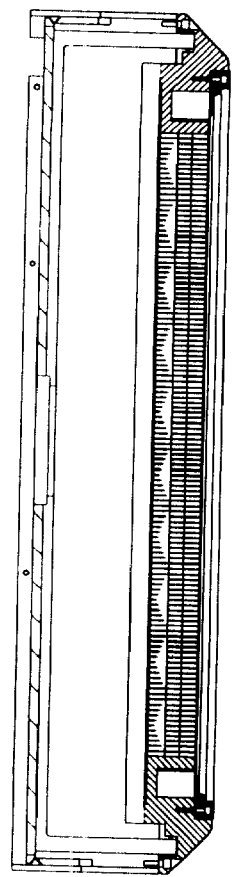
FIGS. 2d and 2e illustrate cross-sectional views of the detector head in which the array of detector blocks is optically coupled to a photodiode array.
Figure 2D:
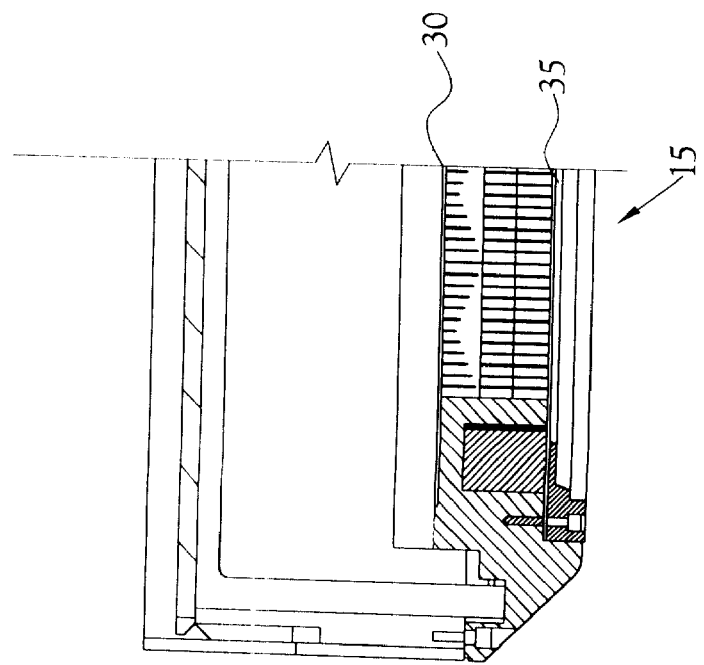

The present invention is a scintillation detector array for encoding energy, position and time coordinates of gamma ray interactions for use in Single Photon Emission Computed Tomography, ("SPECT"), with or without coincidence photon imaging, Planar Imaging, and Positron Emission Tomography, ("PET"), imaging. Referring now to the drawings, FIG. 1 depicts a perspective view of a medical imaging scanner 12 embodying scintillation detector arrays 10 for encoding the energy, position and time coordinates of gamma-ray interactions. The detector head assembly 15 comprises an (n)×(m) array of detector blocks 20, optically coupled to an (q)×(p) array of photomultiplier tubes (PMTs) 25 in one embodiment of the design; or to an (y)×(z) array of optical detectors such as Avalanche Photodiodes (APDs) or PIN Photodiodes 25' in another embodiment of the design. Note the variables (n),(m),(q),(p),(y),(z), may or may not equal each other. FIG. 2a depicts an 8×10 array of detector blocks 20 optically coupled to a 9×11 array of photomultiplier tubes 25 configured so that the center of each PMT 25 resides over the corner of each detector block 20. While this is the preferred arrangement, where the variables (n),(m),(q),(p),(y),(z) are equal the scintillator elements and the optical detectors can be positioned so as to be co-linear. As seen in FIGS. 2b and 2c, the PMTs 25 are partitioned into 99 square compartments using 0.25 mm thick magnetic shielding arranged in a cross pattern to form a grid that locates the PMTs 25 and provides structural support for the 1.0 mm glass window 30 that separates the PMTs 25 from the detector blocks 20. An hermetic enclosure is provided by a thin stainless steel foil 35 membrane mounted to the subject side of the enclosure. As seen in FIGS. 2d and 2e, a similar arrangement is utilized when the optical detector is a photodiode array.

FIG. 3 (a) is a perspective view of a detector block 20 from the detector head 15 of FIG. 2 for one preferred embodiment of the design incorporating discrete scintillators 40 composed of two stacked different scintillator materials, i.e. a slow scintillator material 140 and a fast scintillator material 240, respectively, of different decay times optically coupled to a segmented inverted light guide. Those skilled in the art will appreciate that the light guides discussed herein can be either "active" or "non-active". The term "non-active" is used when the light guide is composed of a non-scintillating material, whereas an active light guide is composed of scintillating material. The use of an active light guide has the inherent characteristic of mispositioning of events which occur as a result of interactions in the non-segmented portion of the light guide. Provided the active light guide is properly designed the magnitude of mispositioned events can be minimized, but never completely eliminated. In the preferred embodiment, light guide 50 is non-active.

Moreover, the term "segmented", as used herein, describes a plurality of barriers defining a preselected number of slots, the number of which and the depth of which are varied to control the variable statistical distributions of photons, whereas non-segmented light guides are continuous such as those used in conventional gamma cameras. And, as used herein, the term "inverted" is used to describe a light guide in which the slotted section of the light guide is optically coupled to the optical detectors, whereas for a traditional (non-inverted) light guide the section of the light guide that contains the non-slotted continuous region is optically coupled to the optical detectors.

The selection of type and orientation of the light guide is in response to various manufacturing constraints. For example when the scintillator and light guide are composed of different materials they may have to be processed separately each using a unique set of tooling and chemical processing. Whereas when the scintillator and light guide are composed of the same material then the tooling and chemical processing are generally the same and no bonding agents are required to optically bond the scintillator to the light guide, since under this circumstance the light guide is cut into the scintillator. However, the detector designer may choose to put an optical bond between the scintillator and the light guide even though they are composed of the same material for the purpose of depth of interaction encoding by either pulse shape or pulse height discrimination. One reason why the detector designer may not want to use the scintillator as an active light guide is due to the mispositioning of events which occur as a result of interactions in the non-segmented portion of the light guide.

For an (n)×(m) array of discrete scintillators 40 optically coupled to a segmented light guide, such as light guide 50, the cut depths for an inverted and non-inverted light guide are unique and are not interchangeable. A detector design incorporating discrete scintillators 40 and a non-inverted light guide, such as non-inverted light guide 150 in the Figures, cannot be converted to a functional inverted light guide detector of equivalent performance simply by flipping the light guide.

Figure 3A:
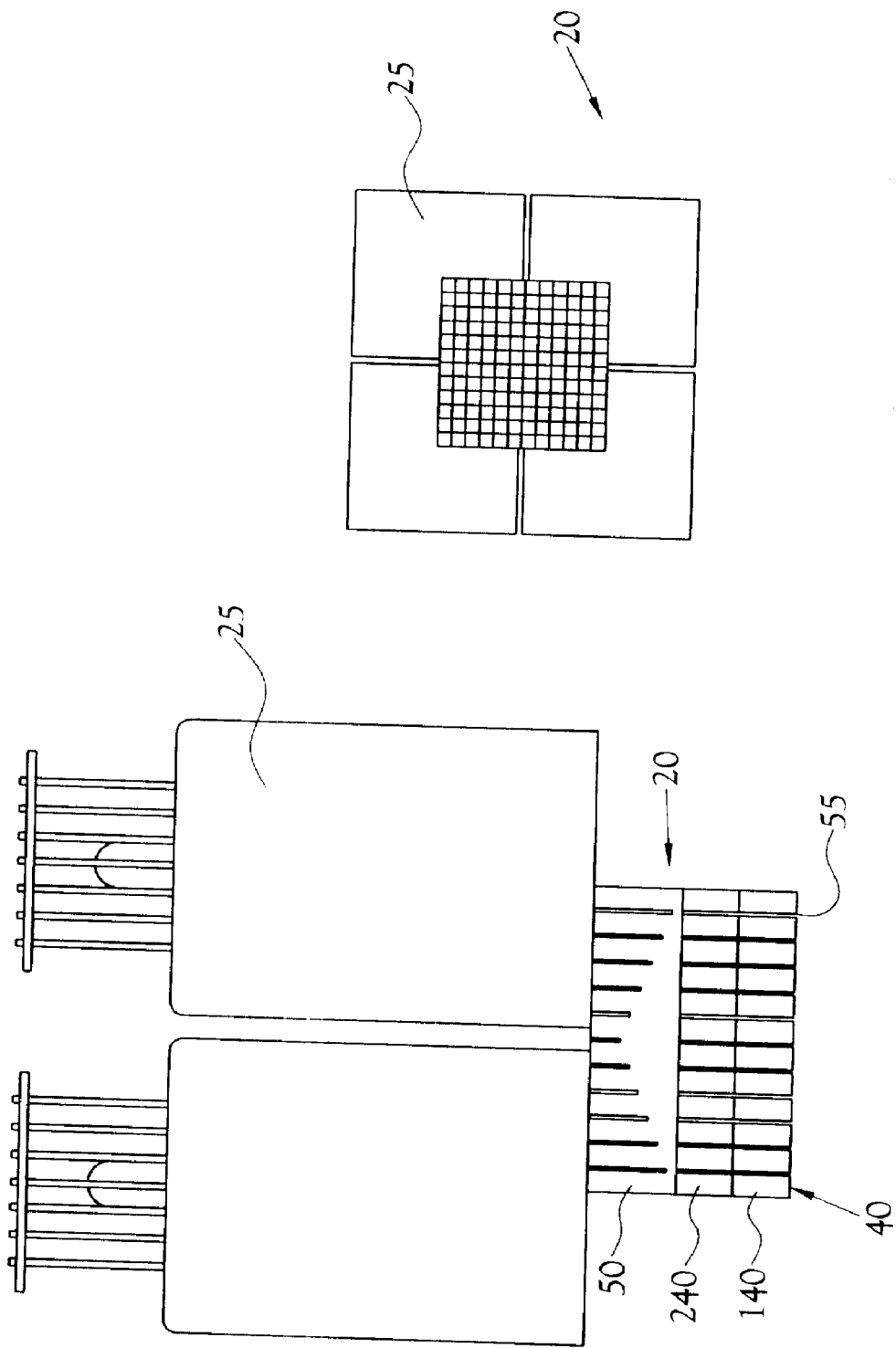
FIG. 3(a) is a perspective view of one detector block from the detector head illustrated in FIG. 2 for one preferred embodiment of the design incorporating discrete scintillators composed of two stacked different scintillator materials of different decay times optically coupled to a non-active segmented inverted light guide which is optically coupled to photomultiplier tubes (PMTs). The PMTs are the optical detectors.

For the preferred embodiment of the design, an inverted segmented light guide 50, which is non-active, is used as depicted in FIG. 3(a). The composition of the inverted segmented light guide 50 can be of any material that is chemically compatible with the scintillator material and is optically transmissive to the wavelength of emission of the scintillator. Other material properties constraints the detector designer must consider in selection of the light guide material is the index of refraction, thermal characteristics, mechanical characteristics and cost. As stated above, in the preferred embodiment, the inverted segmented light guide 50 was designed to be non-active so that mispositioning of events due to gamma-ray interactions in the light guide would not occur. The light guide was designed to be inverted so that registrational tolerances could be eased with respect to the correspondence of the discrete scintillator elements 40 relative to the partitioned section of the light guide. The reflector may be of any material that has high reflectance for the emission wavelength of the scintillator(s). In the case of NaI(Tl) and LSO, 1.53 micron Silicon dioxide ($SiO_2$) was selected as the reflector. Other particle diameters could be used with the general trend as the particle diameter increases the optical cross-talk among the discrete scintillator elements as well as among the partitions of the light guide increases thereby degrading the signal-to-noise ratio.

Two different scintillators 140 and 240 having different decay times are used in one of the preferred embodiments of the design as illustrated in FIG. 3(a). NaI(Tl) was selected as the scintillator of choice for the SPECT measurements and is the current industry standard. The NaI(Tl) block size is 52 mm×52 mm×10 mm thickness. Block sizes of different cross sections or thickness can be selected by the detector designer; the cross-section will be set by the dimensions of the optical detector(s) and the thickness based on the level of compromise between efficiency gain and resolution degradation. Prior to sawing the NaI(Tl) into segments it must be bonded to a substrate for mechanical integrity during processing and to preserve the discrete elements positional registration. Selection of the bonding agent and substrate requires consideration of mechanical, chemical, and optical properties. The bonding agent and substrate must be optically transmissive to the emission wavelength of the NaI(Tl) scintillator, they must be chemically compatible and provide mechanical strength without thermal expansion detriment. An optical glass slide of 0.5 mm thickness was selected as the bonding substrate. Other glass slide thicknesses could be selected based on the level of compromise among mechanical strength, optical cross-talk, and optical attenuation. The bonding agent may be either epoxy or RTV. Selection of the 'sawing' method for segmentation must consider thermal and mechanical stresses as well as chemical compatibility. NaI(Tl) processing should be performed in a dry room to prevent hydration of the scintillator. The cutting lubricant temperature must be controlled to prevent thermal fracture of the scintillator; further it must be chemically compatible so that the mechanical dimensions and optical properties of the scintillator do not change with time. Regardless of which cutting method or lubricant is selected all residues from the process must be removed from the scintillator surface otherwise the total light emitted will be reduced. A low viscosity oil similar in viscosity to water was selected as the cutting lubricant. Residues from the cutting process were subsequently removed either chemically or mechanically.

The 52 mm×52 mm×10 mm NaI(Tl) block was bonded to a 0.5 mm thick glass substrate and sawed into a 12×12 discrete element array of 4.37 mm pitch and 4.0 mm×4.0 mm×10.0 mm crystal size. Silicon dioxide powder of 1.53 micron particle size is used as the reflector in the interstices 55 of the 144 elements of the array and is also used as the reflector between the blocks and on the scintillator non-interstitial surfaces. The silicon dioxide reflector in the interstices 55 is 'sealed' with a small layer of Teflon powder. This is to prevent the permeation of bonding agents into the silicon dioxide reflector from subsequent bonding processes.

Referring to FIG. 3($a$). LSO was selected as the other scintillator of the pair due to its high luminosity, high density, effective-Z and its fast decay time (see Table 1).

TABLE 1

Properties of Proposed PET Scintillators

|  | NaI(Tl) | BGO | LSO | LOP | GSO | $CeF_3$ | $BaF_2$ |
|---|---|---|---|---|---|---|---|
| Density (gm/$cm^3$) | 3.67 | 7.13 | 7.4 | 6.53 | 6.71 | 6.16 | 4.89 |
| Effective Z | 50.6 | 74.2 | 65.5 | 62.5 | 58.6 | 52.7 | 52.2 |
| Mean Free Path (cm)* | 2.93 | 1.05 | 1.16 | 1.37 | 1.43 | 1.71 | 2.20 |
| Index of Refraction | 1.85 | 2.15 | 1.82 | 1.7 | 1.91 | 1.68 | 1.56 |
| Hydroscopic? | YES | NO | NO | NO | NO | NO | Slight |
| Rugged? | NO | YES | YES | YES | NO |  |  |
| Decay Time (ns) | 230 | 300 | 40 | 24 | 60 | 27 | 0.6 |
| Emission Peak (nm) | 410 | 480 | 420 | 360 | 440 | 340 | 220 |
| Light Output [NaI(Tl) = 100] | 100 | 15 | 75 | 32 | 25 | 4–5 | 5 |
| Energy Resolution* | 7.8 | 10.1 | 10.1 |  | 8.9 | 20 | 11.4 |
| Photoelectric Fraction* | .175 | .411 | .324 | .288 | .247 | .188 | .186 |
| Incoherent Fraction* | .790 | .543 | .629 | .670 | .712 | .778 | .779 |
| Mass Attenuation ($cm^2$/gm)* | .0930 | .1332 | .1170 | .1118 | .1040 | .0951 | .0929 |
| Mass Energy Absorp ($cm^2$/gm)* | .0409 | .0731 | .0601 | .0553 | .0495 | .0424 | .0414 |
| Linear Attenuation ($cm^{-1}$)* | .3411 | .9496 | .8658 | .7302 | .6978 | .5858 | .4545 |
| Linear Energy Absorp ($cm^{-1}$)* | .1501 | .5214 | .4447 | .3612 | .3323 | .2614 | .2024 |
|  | $PbSO_4$ | $PbCO_3$ | LAP[1] | LuAG[1] | YSO[4] |  |  |
| Density (gm/$cm^3$) | 6.2 | 6.6 | 8.34 | 6.9 | 4.543 |  |  |
| Effective Z | 73.1 | 75.9 | 63.9 | 61.7 | 34.2 |  |  |
| Mean Free Path (cm)* | 1.22 | 1.10 | 1.05 | 1.31 | 2.58 |  |  |
| Index of Refraction | 1.88 | 1.8 |  |  | 1.8 |  |  |
| Hydroscopic? | NO | NO | NO | NO | NO |  |  |
| Rugged? |  |  | YES | YES | YES |  |  |
| Decay Time (ns) | 136 | 8.5 | 11[2] | 58[3] | 70 |  |  |
| Emission Peak (nm) | 350 | 475 | 390 | 500 | 420 |  |  |
| Light Output [NaI(Tl) = 100] | 9 | 1.4 | 17 | 25 | 118 |  |  |
| Energy Resolution* | 40 | 42 |  | 14.9 | 8.0 |  |  |
| Photoelectric Fraction* | .399 | .432 | .305 | .277 | .051 |  |  |
| Incoherent Fraction* | .556 | .520 | .651 | .683 | .927 |  |  |
| Mass Attenuation ($cm^2$/gm)* | .1320 | .1382 | .1141 | .1105 | .0853 |  |  |
| Mass Energy Absorp ($cm^2$/gm)* | .0718 | .0775 | .0574 | .0540 | .0315 |  |  |
| Linear Attenuation ($cm^{-1}$)* | .8181 | .9122 | .9515 | .7623 | .3875 |  |  |
| Linear Energy Absorp ($cm^{-1}$)* | .4449 | .5113 | .4790 | .3727 | .1431 |  |  |

*at 511 Kev
[1]Computed 10-Feb-1995
[2]60% @ 11 nsec, 26% @ 28 nsec, 13% @ 835 ns
[3]13% @ 58 nsec, 21% @ 310 nsec, 65% @ 2090 nsec
[4]Computed 5-Jan-1996

LSO is a rugged scintillator and its processing methods are unique and different from NaI(Tl). Preferably, the 52 mm×52 mm ×10 mm LSO block is either mechanically polished or etched to transparency prior to bonding or sawing. The reason the mechanical and/or etch process is used is to maximize the transmission of the other scintillator's light through the LSO and the light guide 50. This mechanical polishing or etching to transparency condition also applies to the light guide. Those skilled in the art will recognize that while polishing or etching to optical transparency is preferred, a polish or etch that results in less than optical transparency may alleviate certain manufacturing problems associated with etching to optical transparency. However, polishing or etching to less than optical transparency reduces the efficiency of the detector and/or light guide. Pyrophosphoric acid ($H_4P_2O_7$) is used as the chemical etchant for LSO. Etching LSO to transparency is a function of time and acid temperature. Typically a temperature of 300° C. with approximately 15 minutes duration is required to etch LSO to transparency, other temperatures and durations may also be used to the same effect. One problem associated with this etching temperature is thermal stress which can fracture the scintillator. Thermal stress can be minimized by having the scintillator and the acid at the same temperature during the etch process. Upon removal of the LSO from the etch bath it is allowed to air cool to 100° C. whereupon the LSO is submerged in boiling water to rinse the residual pyrophosphoric acid from the LSO surface. Upon removal of the LSO from the boiling water rinse bath it is allowed to air dry to room temperature. The LSO is then submerged in a 37% Hydrochloric acid (HCl) bath for approximately 2 minutes to remove residual pyrophosphoric acid from the LSO which was not removed by the boiling water rinse. The duration of the HCl rinse is not critical as it will not etch the LSO, it will only remove surface contaminants. Following the HCl etch a clean water rinse is used to remove residual HCl from the LSO surface.

The mechanically polished and/or etched uncut LSO block is optically bonded to a mechanically polished optical grade glass or ultraviolet transmissive plastic whose dimensions are 52 mm×52 mm×12.7 mm thickness. Other thicknesses can be used depending on the desired statistical distribution of photons and optical transmission and optical attenuation compromise. The light guide 50 can be cut or uncut prior to bonding to the LSO, the choice really depends upon the fabrication processes selected. The end result should yield the desired discrete element registration to light guide partition.

The 52 mm×52 mm×10 mm LSO block is cut into a 12×12 element array of 4.37 mm pitch and 4.0 mm×4.0 mm×10 mm crystal size. The cut LSO crystal array must be etched to remove surface contaminants due to the sawing process. This etch is generally not designed to be optically transparent since the etch at that temperature would be detrimental to the optical bond. Cleaning the crystal surface can be accomplished with an HCl etch as stated above. However enhancing the LSO light output after the sawing process requires an HCl etch to remove the surface contaminants from the sawing process followed by a pyrophosphoric acid etch at a nominal temperature of 170° C. for a duration of approximately 20–30 seconds. Etching for shorter or longer duration at this temperature will not provide the optimum light yield. Other pyrophosphoric acid temperatures and etch times may be used. The choice depends upon the manufacturing process selected and the amount of time allocated to the etch process and the desired light output. The pyrophosphoric acid etch removes the sawing process induced micro-fracturing of the LSO crystal surface which would otherwise trap the LSO luminescence light. The pyrophosphoric acid etch is followed by a 100° C. water rinse then a second HCl rinse followed by a room temperature water rinse.

The interstices 55 of the cut LSO and light guide arrays are preferably filled with silicon dioxide powder of 1.53 micron particle size to serve as reflector. It will be recognized that other reflector materials, such as titanium dioxide, aluminum oxide, magnesium oxide, barium sulfate, zinc oxide and Teflon powder, can also be utilized as reflectors. A small layer of Teflon powder is then used to 'seal' the Silicon dioxide reflector in the interstices of the arrays. This is to prevent permeation of bonding agents into the reflector from subsequent bonding processes. The LSO side of the LSO/light guide array is then optically bonded to the glass substrate of the NaI(Tl) array.

Two prototype detectors were fabricated using the methods described above. Testing of the prototype detectors required that the NaI(Tl) array be hermetically sealed. For the one prototype an aluminum housing was used to hermetically seal the NaI(Tl) array only. Glass was used as the hermetic seal for the second prototype, however, in this case the NaI(Tl), LSO and light guide were all enclosed.

Referring to FIGS. 3a–3l, various configurations of detector arrays are illustrated. It should be understood that the figures are not drawn to scale. These figures present a perspective view of the types of detector blocks which could be incorporated in the detector head 15 illustrated in FIG. 2. In the various embodiments illustrated herein, the scintillator can either be a single layered scintillator or can be composed of two stacks of scintillator material of different decay times either using the same scintillator material in each layer or different scintillator materials. Selection of the scintillator material for each scintillation layer is application dependent. Table 1 herein provides examples of various scintillator materials, but is not all inclusive. Other scintillator materials having similar properties or other application dependent properties could also be substituted. The embodiments can be further modified by varying the types of optical detectors which are used, i.e. photomultipliers and/or photodiodes. An additional variant is whether or not a segmented optical light guide is used. If a segmented optical light guide is used then the variant is whether the configuration is inverted or non-inverted.

Figure 3B:
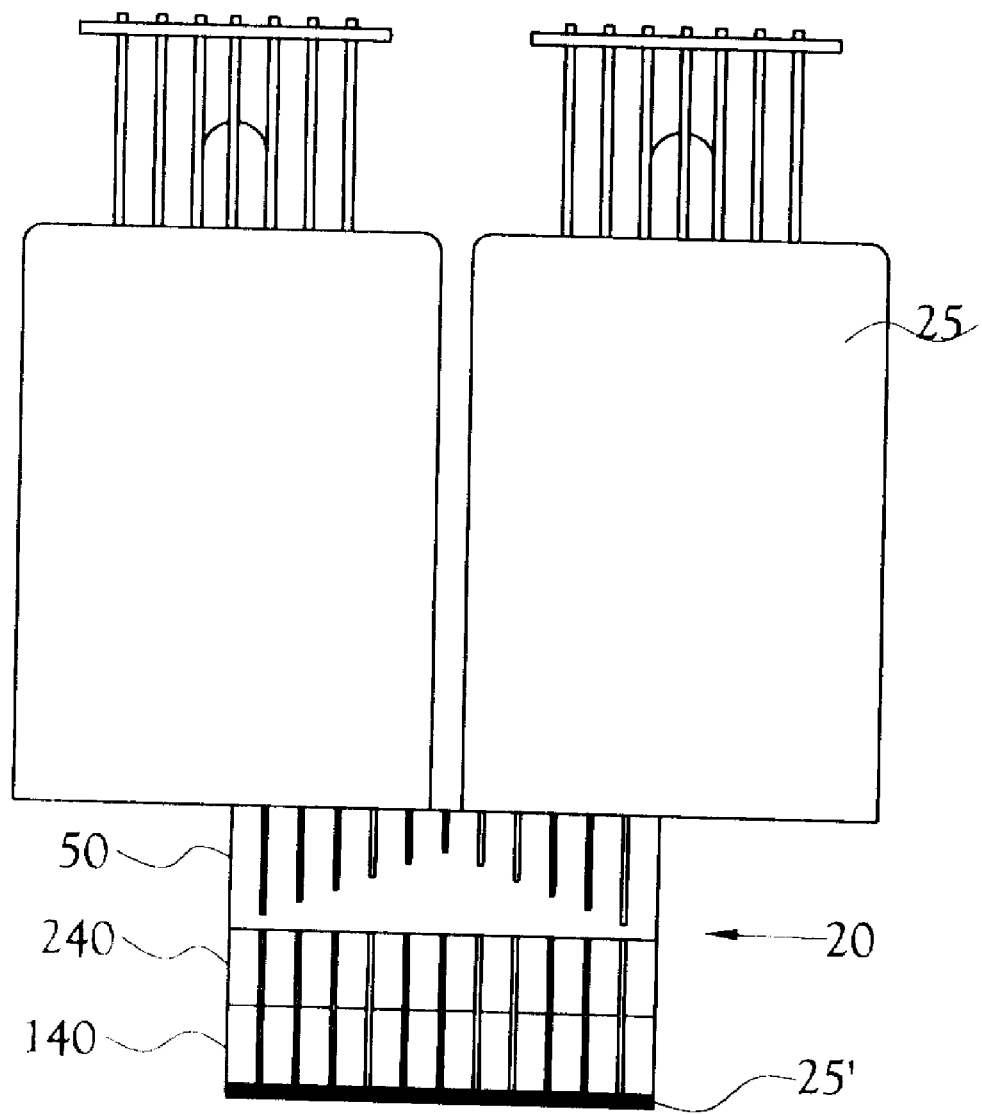
FIG. 3(b) is a perspective view of one detector block from the detector head illustrated in FIG. 2 for another embodiment of the design incorporating discrete scintillators composed of two stacked different scintillator materials of different decay times optically coupled to a non-active segmented inverted light guide. The light guide is optically coupled to PMTs in addition a photodiode array is optically coupled to one of the scintillator arrays. The PMTs and photodiode arrays are the optical detectors.

In this regard, in FIG. 3(a) one detector block 20 from the detector head 15 illustrated in FIG. 2 incorporates discrete scintillators 40 composed of two stacked different scintillator materials 140 and 240 of different decay times optically coupled to a segmented inverted light guide 50, which is preferably non-active, which in turn is optically coupled to photomultiplier tubes (PMTs) 25. The PMTs 25 are the optical detectors. This embodiment can be further varied, as shown in FIG. 3(b) with the addition a photodiode array 25' which is optically coupled to one of the scintillator arrays 20. The PMTs 25 and photodiode arrays 25' are the optical detectors.

Figure 3C:
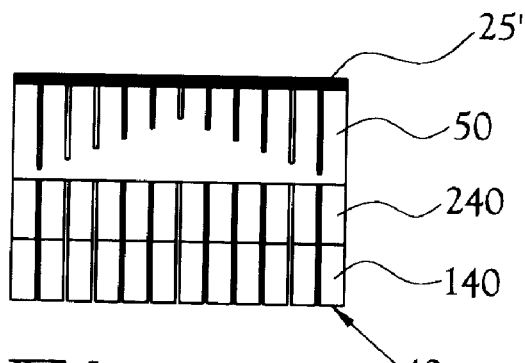
FIG. 3(c) is a perspective view of one detector block from the detector head illustrated in FIG. 2 for another embodiment of the design incorporating discrete scintillators composed of two stacked different scintillator materials of different decay times optically coupled to a non-active segmented inverted light guide. The light guide is optically coupled to a photodiode array. The photodiode array is the optical detector.
Figure 3D:
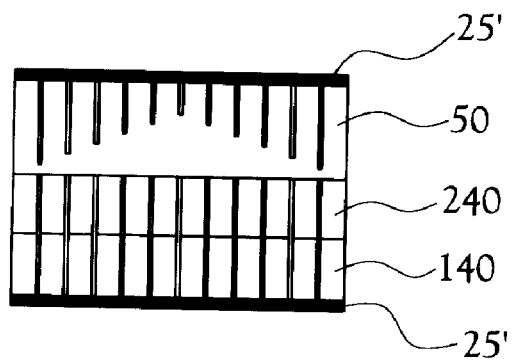
FIG. 3(d) is a perspective view of one detector block from the detector head illustrated in FIG. 2 for another embodiment of the design incorporating discrete scintillators composed of two stacked different scintillator materials of different decay times optically coupled to a non-active segmented inverted light guide. The light guide is optically coupled to a photodiode array in addition a second photodiode array is optically coupled to one of the scintillator arrays. The two photodiode arrays are the optical detectors.
Figure 3E:
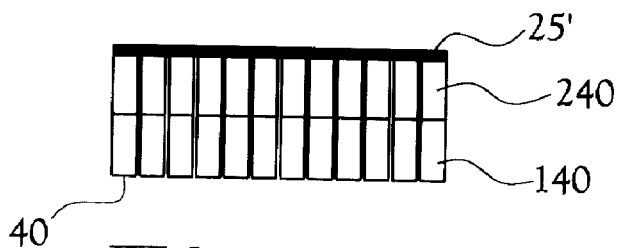
FIG. 3(e) is a perspective view of one detector block from the detector head illustrated in FIG. 2 for another embodiment of the design incorporating discrete scintillators composed of two stacked different scintillator materials of different decay times. One of the two scintillator arrays is optically coupled to a photodiode array. The photodiode array is the optical detector.
Figure 3F:
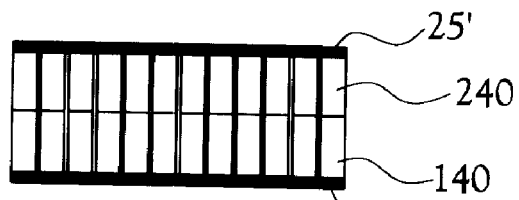
FIG. 3(f) is a perspective view of one detector block from the detector head illustrated in FIG. 2 for another embodiment of the design incorporating discrete scintillators composed of two stacked different scintillator materials of different decay times. One photodiode array is optically coupled to one of the scintillator arrays. A second photodiode array is optically coupled to the other scintillator array. The photodiode arrays are the optical detectors.

Another embodiment is illustrated in FIG. 3(c). This embodiment incorporates discrete scintillators 40 composed of two stacked different scintillator materials 140 and 240 of different decay times optically coupled to a segmented inverted light guide 50, which is preferably non-active. The light guide 50 is optically coupled to a photodiode array 25' which serves as the optical detector. This embodiment can be further modified, as shown in FIG. 3(d) which includes a second photodiode array 25' optically coupled to one of the scintillator arrays. The two photodiode arrays are the optical detectors. As illustrated in FIG. 3(e), the embodiment illustrated in FIG. 3(c) can be further modified by integrating the light guide function in the discrete scintillators 40. In FIG. 3(f), the embodiment illustrated in FIG. 3(e) has been further modified by optically coupling a second photodiode array 25' to scintillator material 140.

FIGS. 3($g_1$) and ($g_2$) yet another embodiment is illustrated. This embodiment incorporates discrete scintillators 40 composed of two stacked different scintillator materials 140 and 240 of different decay times optically coupled to a segmented non-inverted light guide 150, which is preferably non-active. The light guide 150 is optically coupled to PMTs 25.

Figure 3H:
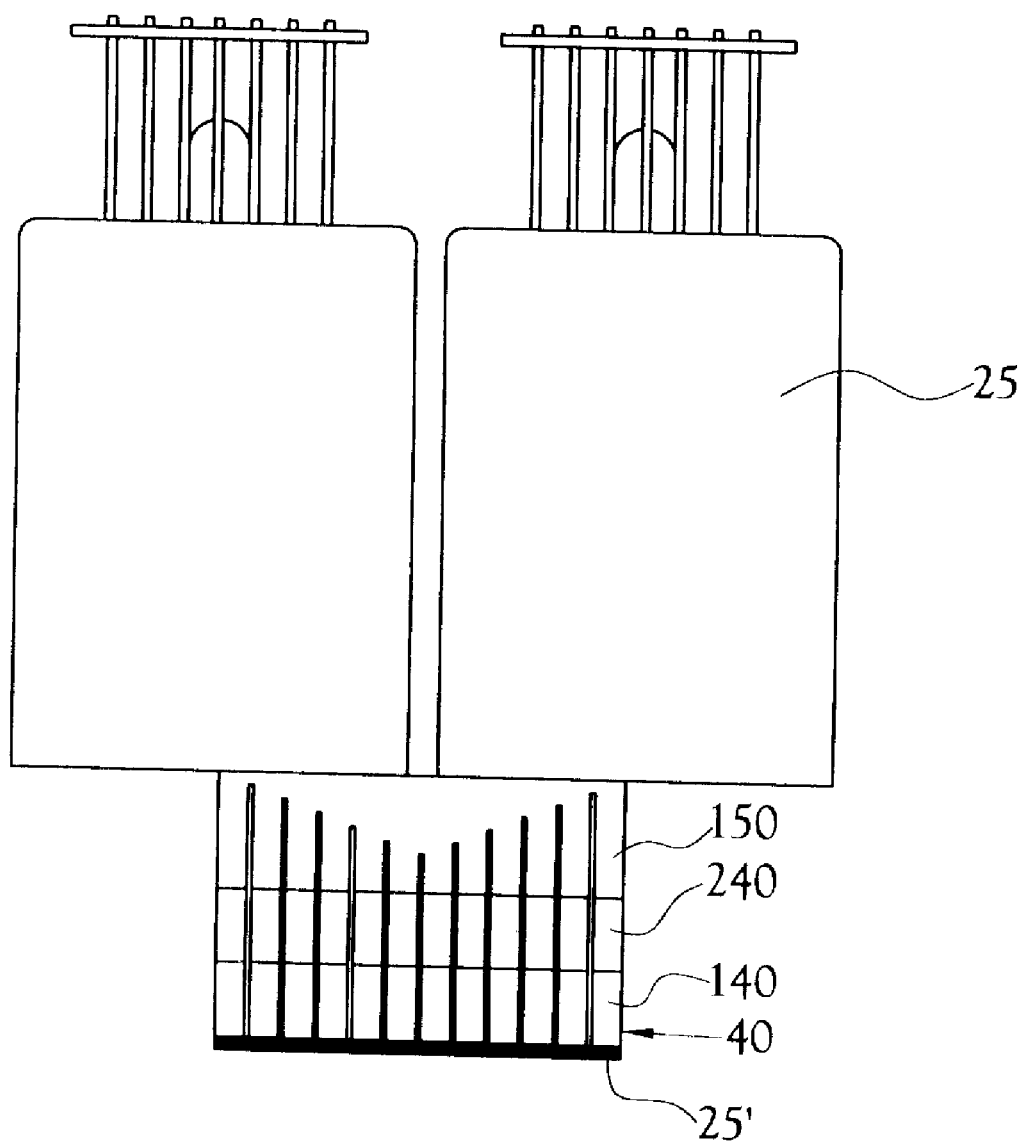
FIG. 3(h) is a perspective view of one detector block from the detector head illustrated in FIG. 2 for another embodiment of the design incorporating discrete scintillators composed of two stacked different scintillator materials of different decay times optically coupled to a non-active segmented non-inverted light guide. The light guide is optically coupled to the PMTs in addition a photodiode array is optically coupled to one of the scintillator arrays. The PMTs and the photodiode arrays are the optical detectors.

FIG. 3(h) illustrates yet another embodiment of the design which incorporates discrete scintillators 40 composed of two stacked different scintillator materials 140 and 240 of different decay times optically coupled to a segmented non-inverted light guide 150, which is preferably non-active. The light guide 150 is optically coupled to the PMTs 25 and in addition a photodiode array 25' is optically coupled to one of the scintillator arrays 140.

Figure 3I:
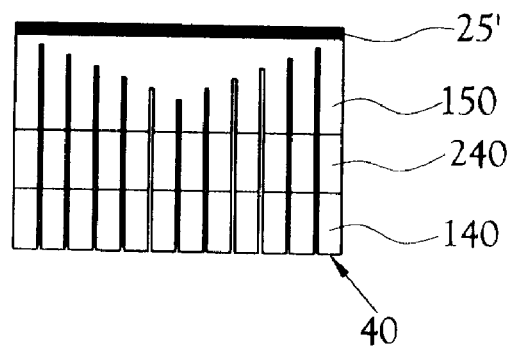
FIG. 3(i) is a perspective view of one detector block from the detector head illustrated in FIG. 2 for another embodiment of the design incorporating discrete scintillators composed of two stacked different scintillator materials of different decay times optically coupled to a non-active segmented non-inverted light guide. The light guide is optically coupled to a photodiode array. The photodiode array is the optical detector.

FIG. 3(i) illustrates still another embodiment of the design incorporating discrete scintillators 40 composed of two stacked different scintillator materials 140 and 240 of different decay times optically coupled to a segmented non-inverted light guide 150 which is preferably non-active. The light guide 150 is optically coupled to a photodiode array 25'. This embodiment can be further modified, by optically bonding layer 140 to a second photodiode array 25'.

Figure 3J:
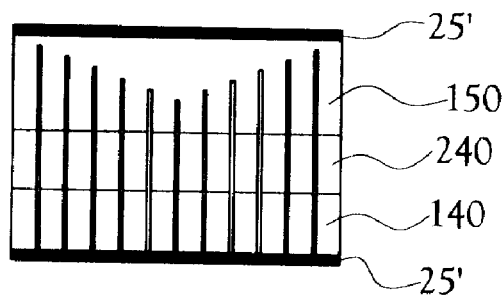
FIG. 3(j) is a perspective view of one detector block from the detector head illustrated in FIG. 2 for another embodiment of the design incorporating discrete scintillators composed of two stacked different scintillator materials of different decay times optically coupled to a non-active segmented non-inverted light guide. The light guide is optically coupled to a photodiode array. A second photodiode array is optically coupled to one of the scintillator arrays. The photodiode arrays are the optical detectors.
Figure 3K:
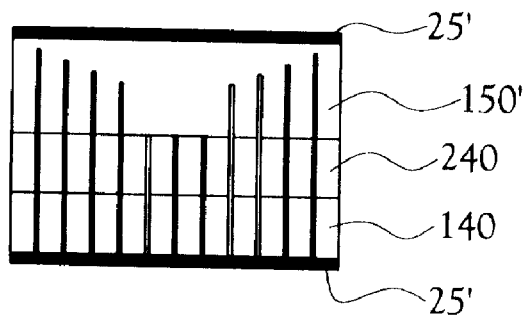
FIG. 3(k) is a perspective view of an alternative detector block applicable to any of the embodiments discussed herein showing that the light depth and configuration of the segmentation is variable depending upon the thickness of the light guide.
Figure 31:
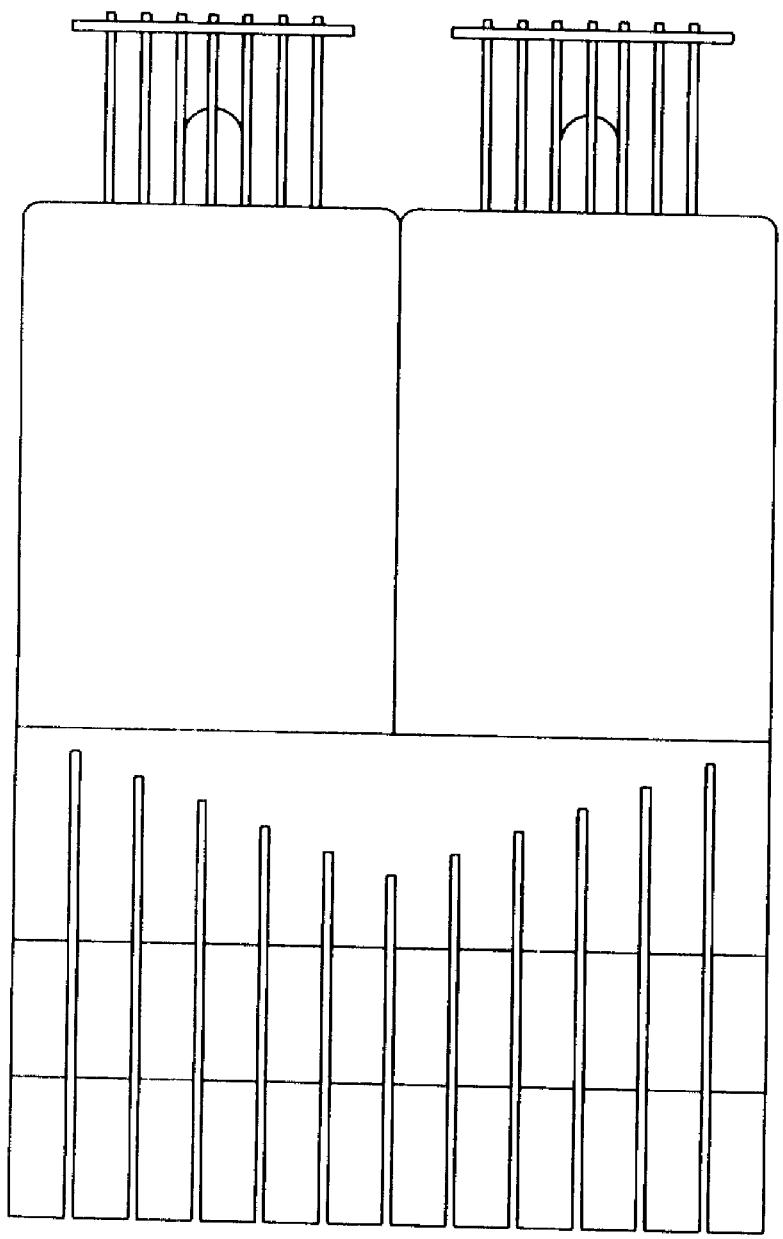
Figure 4A:
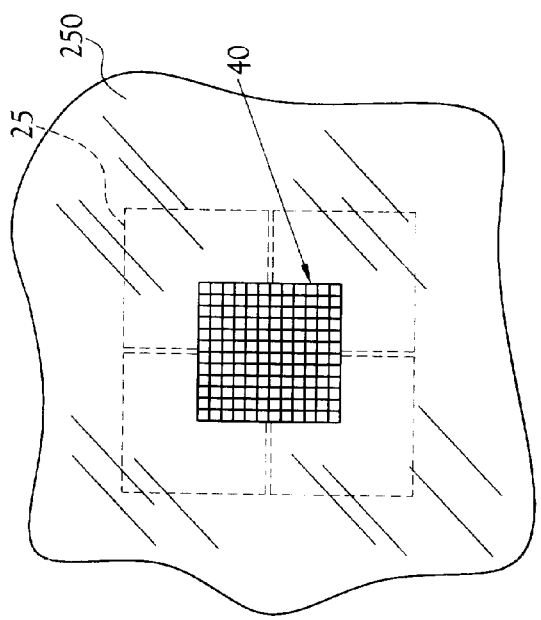
Figure 4B:
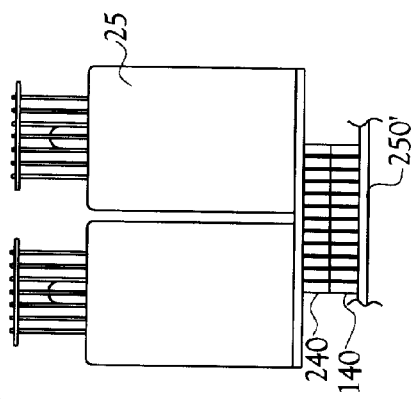
FIG. 4b illustrates an alternate embodiment in which the discrete scintillators are disposed between the light guide and the optical detectors.
Figure 4:
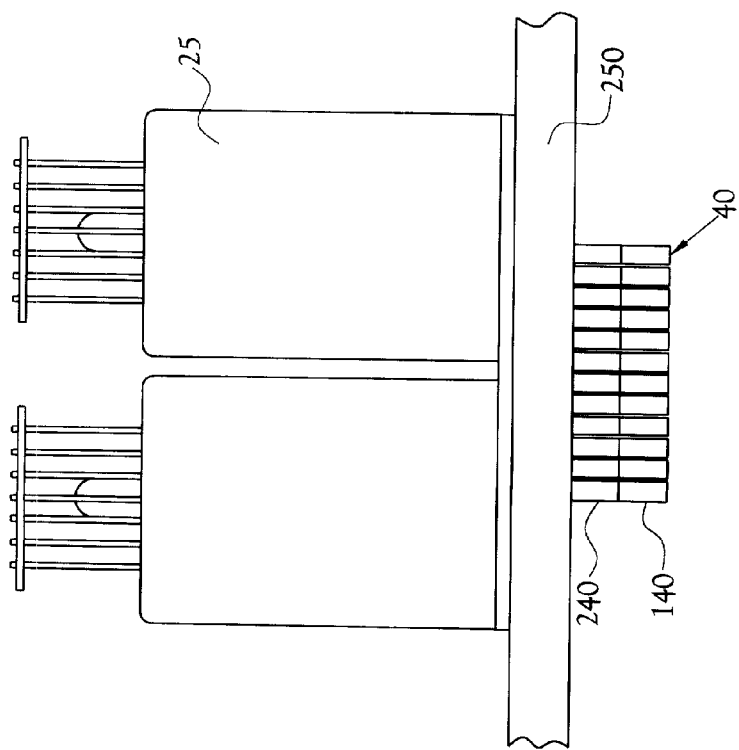
FIG. 4 is inclusive of FIGS. 4, 4a and 4b.

FIG. 3(k) is a perspective view of an alternative segmented light guide 150' from the detector block illustrated in FIG. 3(j) showing that the light depth and configuration of the segmentation is variable depending upon the thickness of the light guide. FIG. 4 illustrates an embodiment of the design incorporating discrete scintillators 40 composed of two stacked different scintillator materials 140 and 240 of different decay times optically coupled to a non-segmented light guide 250, which is preferably non-active. The light guide 250 is optically coupled to the PMTs 25. With respect to each of these embodiments, and the other embodiments described herein, selection of the scintillator material for each scintillation layer is application dependent. Table 1 herein provides examples of various scintillator materials, but is not all inclusive. Other scintillator materials having similar properties or other application dependent properties could also be substituted.

Figure 6A:
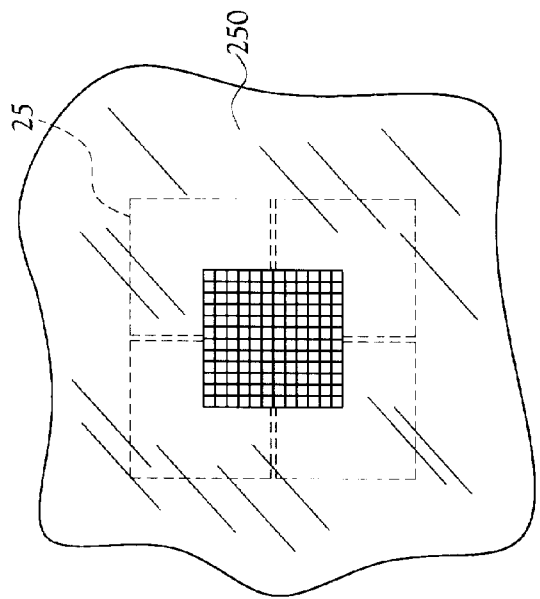
Figure 6B:
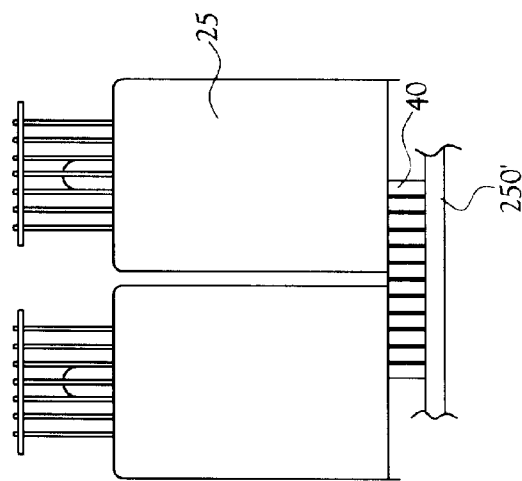
FIG. 6b illustrates an alternate embodiment in which the discrete scintillators are disposed between the light guide and the optical detectors.
Figure 6:
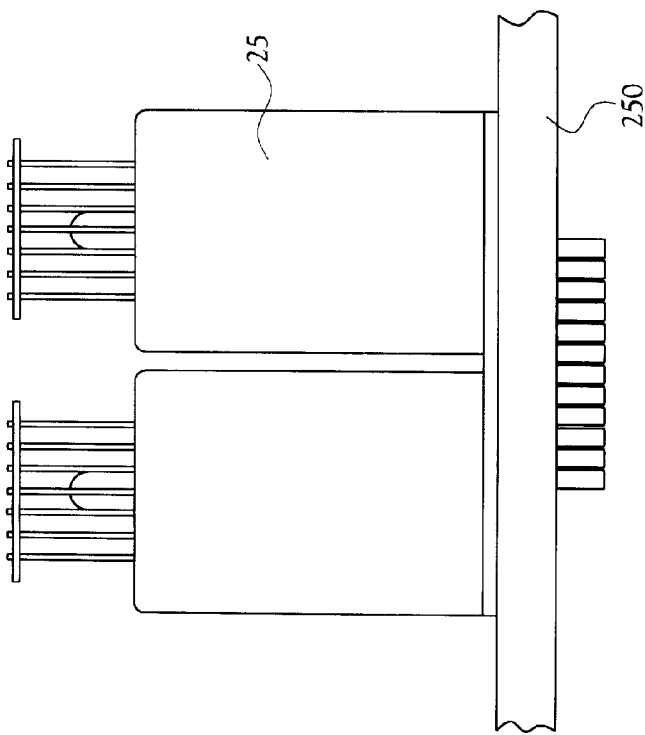
FIG. 6 is inclusive of FIGS. 6, 6a and 6b.
Figure 7:
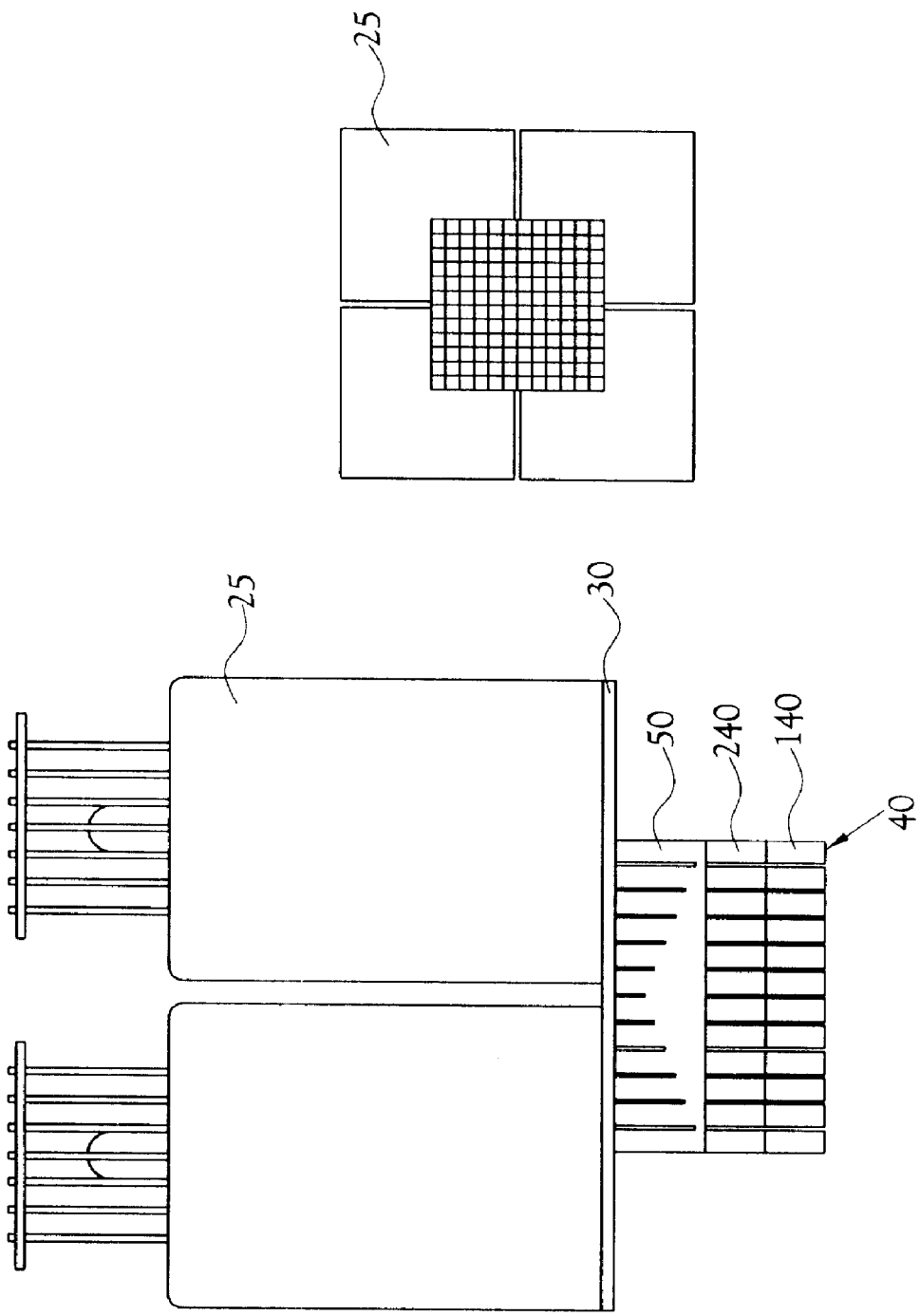
FIG. 7 is a perspective view of one detector block from the detector head illustrated in FIG. 2 for another embodiment of the design incorporating discrete scintillators composed of a single scintillator material of two different decays times optically coupled to a non-active segmented inverted light guide. The light guide is optically coupled to the PMTs. The PMTs are the optical detectors.

As illustrated in FIGS. 4, 6 and 8, in various embodiments, the light guide 250 is continuous, i.e. non-segmented. As illustrated, the continuous light guide 250 has a first surface that extends beyond the interfacing surface of the discrete scintillator elements and has a second surface that extends beyond the interfacing surface of the optical detectors. An alternate embodiment is illustrated in FIGS. 4b and 6b. In this alternate embodiment, the scintillators, which can either be a single layer 40 of material as illustrated in FIG. 6b, or two layers 240 and 140 as illustrated in FIG. 4b, are disposed between the optical detectors 25 and a thin layer continuous light guide 250'. In this regard, the light guide 250', which can either be active or non-active, is disposed on the patient side of the scintillators.

Figure 5:
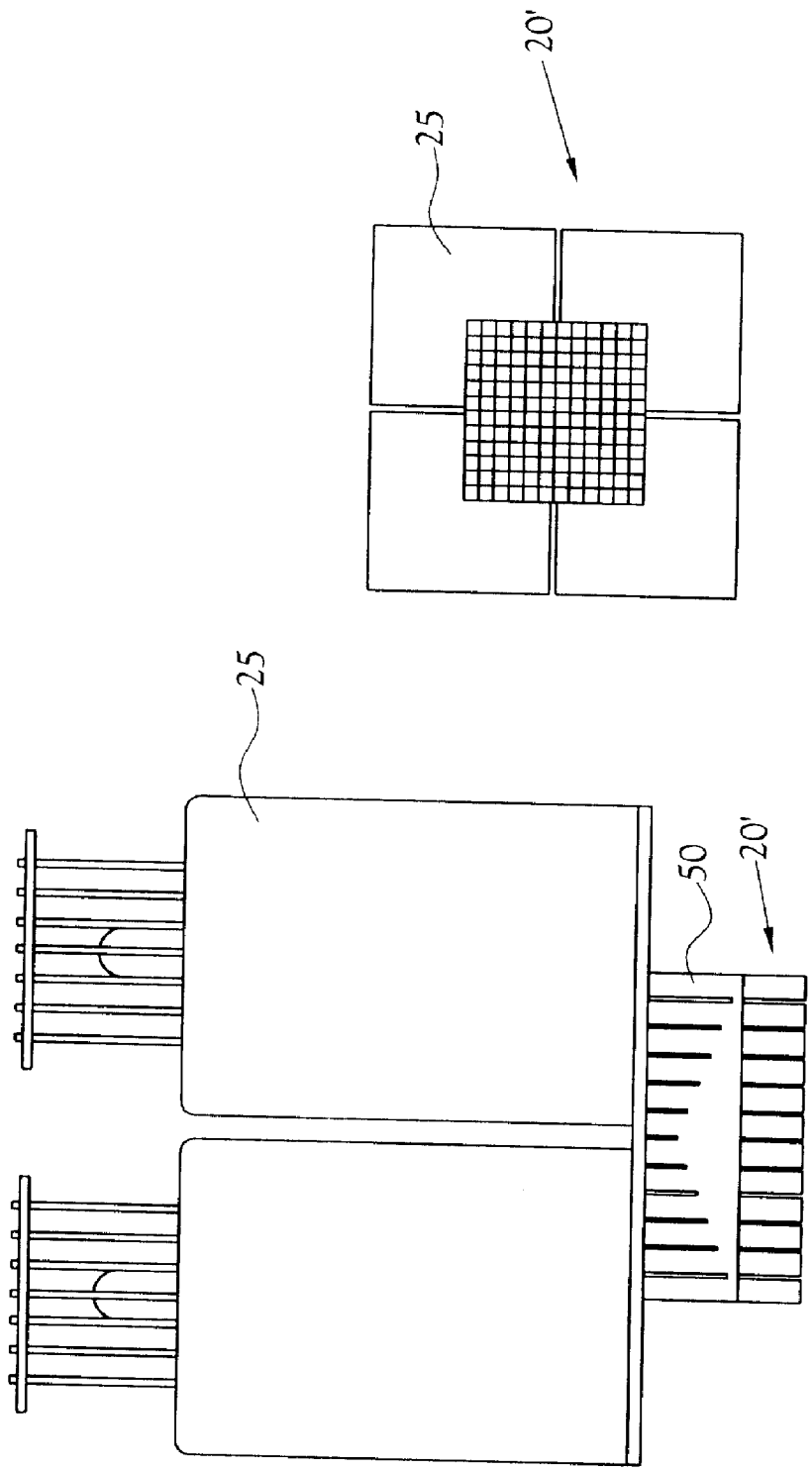
FIG. 5 is a perspective view of one detector block from the detector head illustrated in FIG. 2 for another embodiment of the design incorporating discrete scintillators composed of a single scintillator material optically coupled to a non-active segmented light guide. The light guide may be inverted or non-inverted. The light guide is optically coupled to the PMTs. The PMTs are the optical detectors.
Figure 9A:
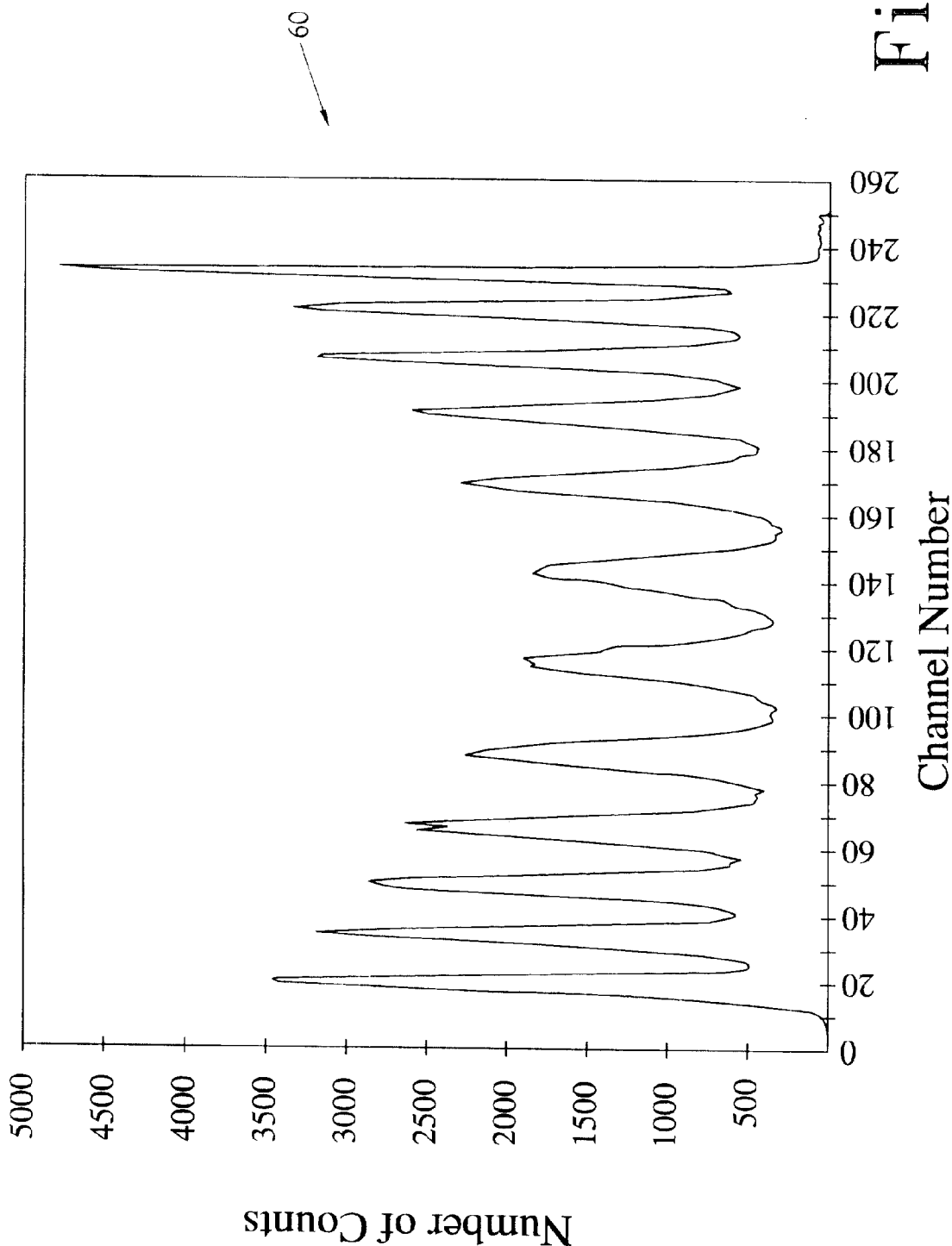
FIG. 9(a) depicts the uniform irradiation by a Na-22 radioactive source at 511 keV of a single layer of NaI(Tl) segmented into a 12×12 array yielding 144 discrete elements. The detector design is exhibited in FIG. 5. The position histogram displayed in FIG. 9(a) is of the overlap of twelve rows each containing 12 discrete scintillator elements. The figure displays excellent peak-to-valleys indicating very good separation among the 144 discrete elements.
Figure 9B:
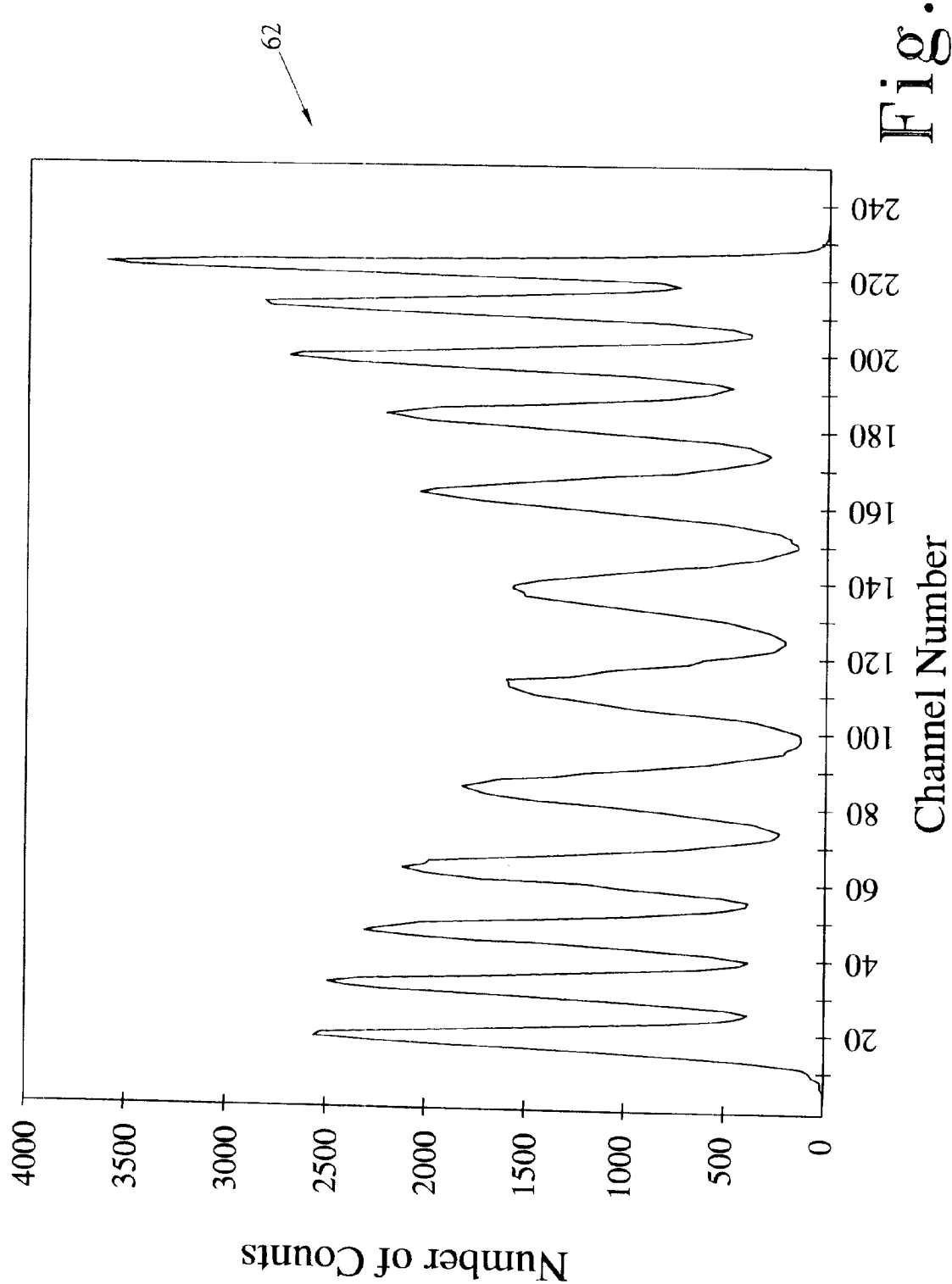
FIG. 9(b) is the same as FIG. 9(a) except Co-57 is used as the radioactive source with a gamma-ray energy of 122 keV.
Figure 10:
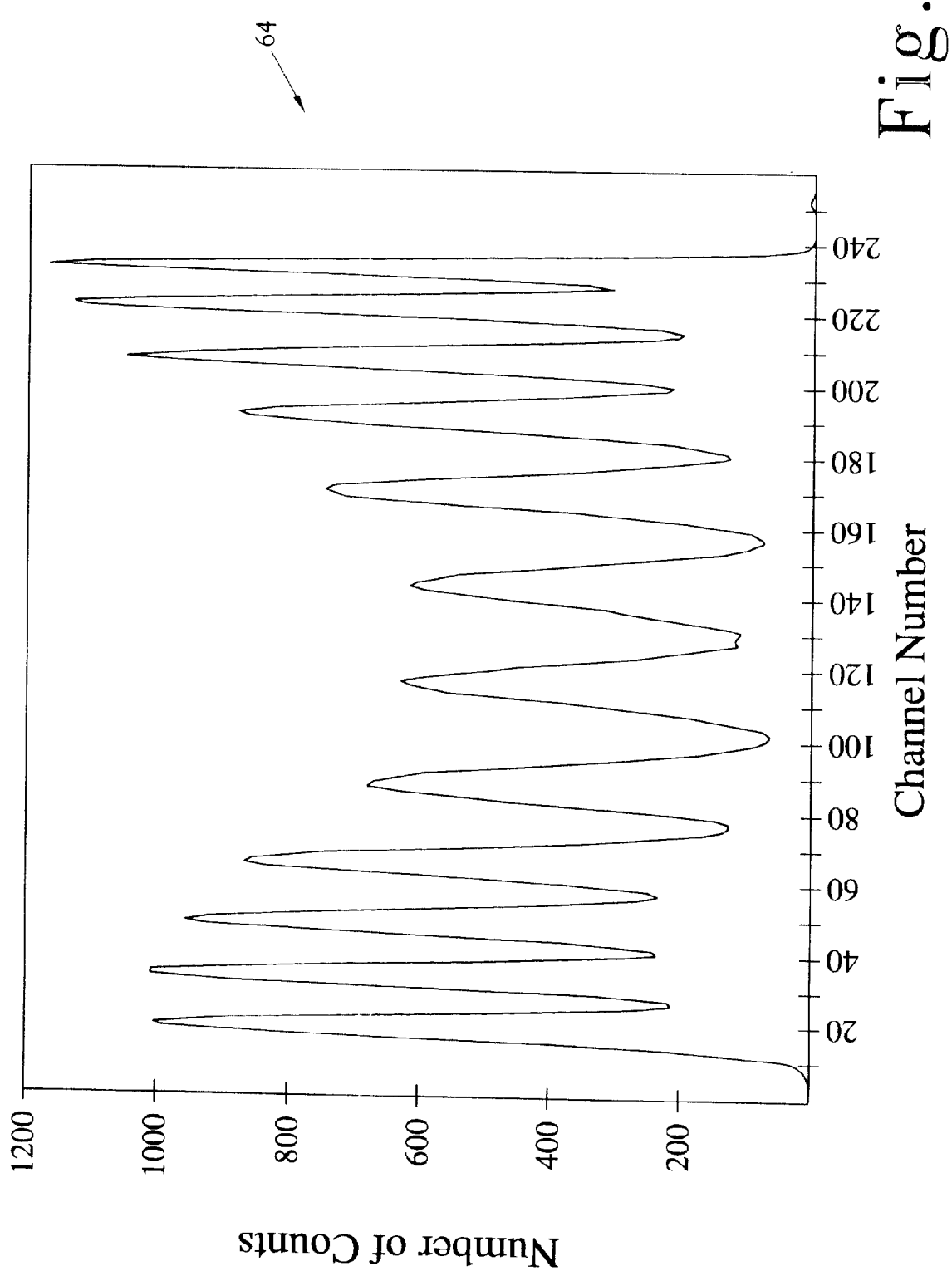
FIG. 10 is the same as FIG. 9(a) except Cd-109 is used as the radioactive source with a gamma-ray energy of 88 keV.

Referring to FIG. 5, the NaI(Tl) array 20' was optically bonded to the segmented inverted light guide 50, which is preferably non-active, for evaluation of the detector design. Testing of the NaI(Tl) array 20' was conducted using standard nuclear spectroscopy instrumentation. The array was evaluated for energy and 'position' space at 511 keV,122 keV and 88 keV, using point sources. The 'position' histograms 60, 62, and 64 for these three energies are provided in FIGS. 9(a), 9(b) and 10, respectively, with Spectra Identification number 27-18-1 .spm. The position histogram as depicted exhibits the overlap of all twelve rows. The twelve position peaks represent all 144 discrete scintillator elements. Any mispositioning of the 144 peaks would result in a degradation of the peak-to-valley. No such degradation is exhibited. The pulse height energy resolution measured at 88 keV, 122 keV, and 511 keV are summarized as follows:

| Energy | Mean Pulse Height Energy Resolution per crystal element |
| --- | --- |
| 88 keV | 9.42% |
| 122 keV | 9.45% |
| 511 keV | 7.57% |

Figure 11:
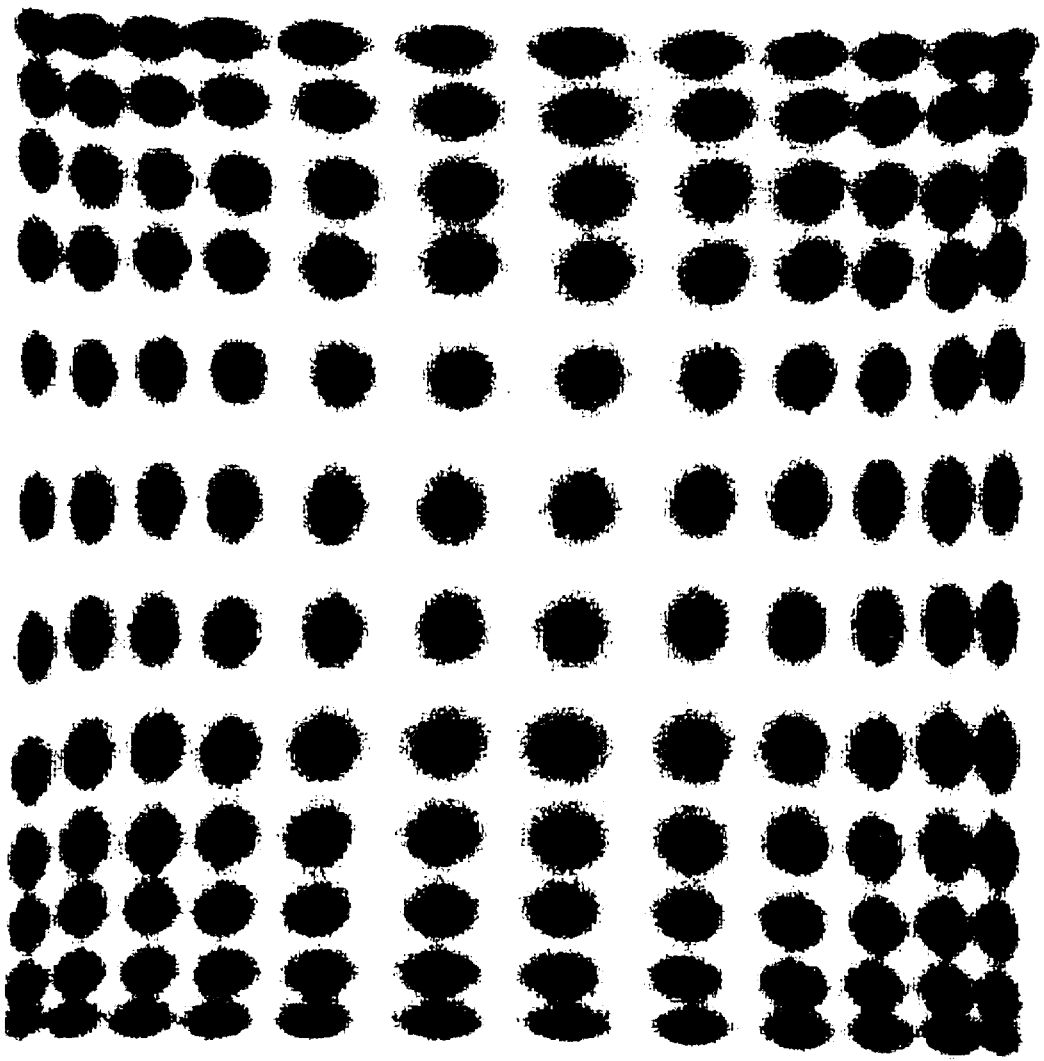
FIG. 11 is the same as FIG. 9(b) except the peak-to-valleys are not displayed. The position histogram displays all 144 discrete NaI(Tl) scintillator elements for the detector design as exhibited in FIG. 5 when uniformly irradiated with 122 keV gamma-rays from Co-57.

FIG. 11 provides position information without the complexity of interpreting twelve overlapped rows. FIG. 11 shows the two dimensional position histogram 66 of the detector design exhibited in FIG. 5 where the scintillator layer is composed of NaI(Tl) layer segmented into the 12×12 array. The light guide 50 is non-active, segmented and inverted. The detector is uniformly irradiated with 122 keV gamma-rays from Co-57. This data indicates that the NaI(Tl) array performance is comparable to existing high resolution SPECT scanners while providing outstanding PET energy, position and time resolution.

Evaluation of the bonded NaI(Tl)/LSO/light guide arrays (see histograms 68 and 70 in FIGS. 12 and 13) requires consideration of the naturally occurring 2.6% abundant Lu-176 element. The Lu-176 is radioactive, producing energetic particles that interact in the scintillator to produce a background count rate of approximately 39 counts per second per gram of LSO scintillator. Due to the high stopping power of LSO very few of the particles originating from the decay of Lu-176 actually escape from the LSO scintillator. Lu-176 background events do not present a problem in PET studies due to their uncorrelated nature, the system labels the events as randoms and are thus rejected. However, the Lu-176 background events which fall into the SPECT energy window are a problem for they are counted as singles and are of the same order of magnitude as the signal rate in many Planar and SPECT studies. FIG. 14 exhibits two energy spectra, one for an LSO crystal irradiated by Cs-137 72, the other spectra is for the Lu-176 background events 74. These spectra indicate standard energy discrimination techniques will not successfully reject Lu-176 background events.

NaI(Tl) and LSO have scintillation decay times of 230 and 40 nanosecs (ns) respectively. For SPECT studies, low energy photons are stopped in the NaI(Tl) crystal(s), producing scintillation events of 230 ns decay time; whereas the Lu-176 background events of LSO are produced with 40 ns decay. The electronics circuitry distinguishes between NaI (Tl) and LSO events based on the decay time signatures of the two scintillators. The technique is known as pulse shape discrimination PSD. Approximately 99% of the Lu-176 background events must be rejected to prevent significant noise counts from occurring in the low count rate SPECT data.

Figure 15:
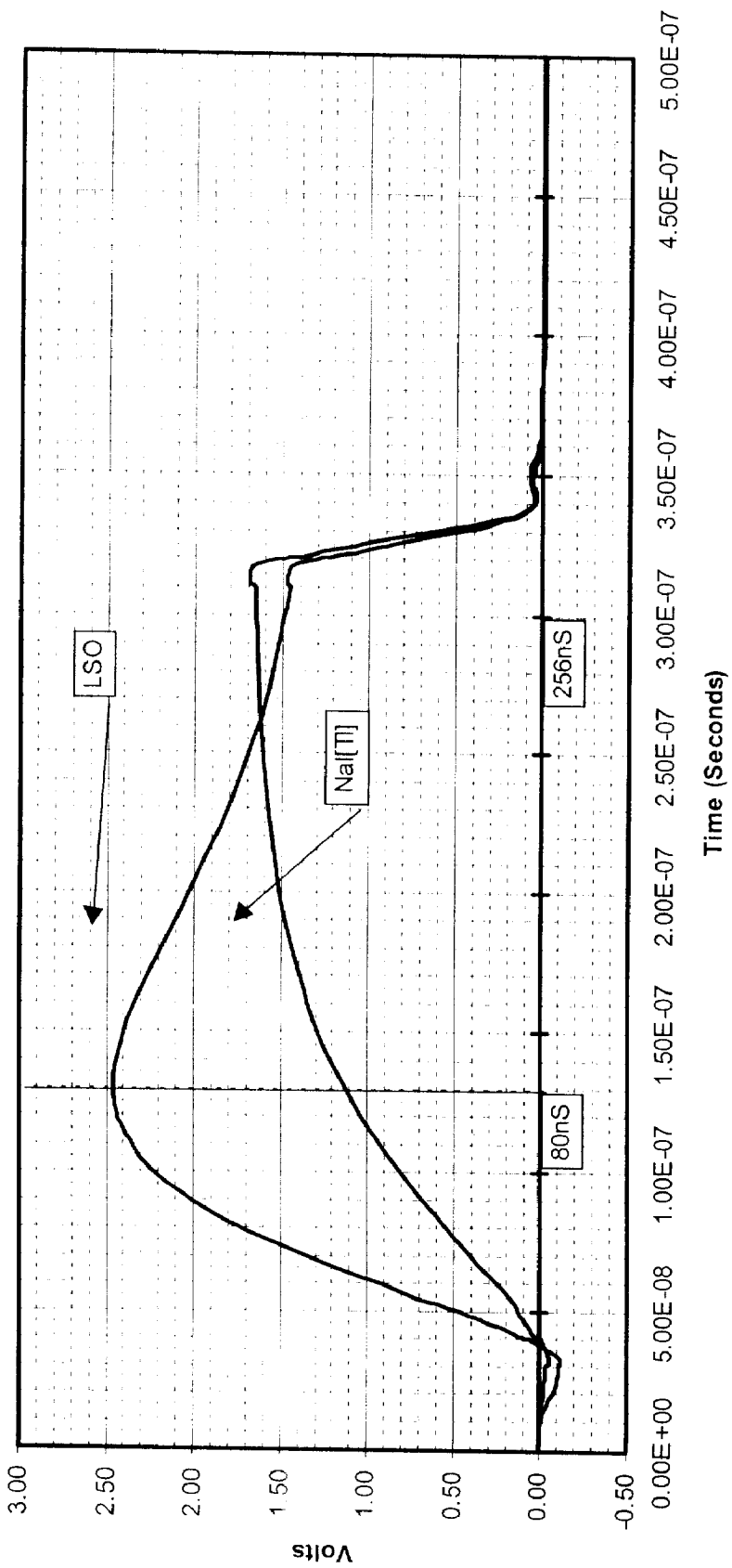
FIG. 15 exhibits the energy integration for NaI(Tl) and LSO. The pulse shape discrimination technique utilized with the detector designs of this disclosure, involves integrating the detector charge at two points in time then ratio the values. For LSO and NaI(Tl) separation the first sample is taken at 80 ns from the start of the integration and the second sample at 256 ns at the end of signal integration to provide a value to normalize out event charge (energy).

The PSD technique utilized in the PET/SPECT detector involves integrating the detector charge at two points in time and then comparing the ratio of the values. For LSO and NaI(Tl) separation, the first sample is taken at 80 ns from the start of the integration and the second sample at 256 ns. The first sample is selected at 80 ns since this is where the maximum difference occurs for the LSO and NaI(Tl) scintillators. The LSO signal will be maximally above the NaI(Tl) signal at 80 ns for a given signal charge. The second sample at 256 ns is at the end of the signal integration to provide a value to normalize out event charge (energy). The two-sample shape discrimination circuit used with the PET/SPECT ASIC does not require additional shape discrimination circuitry inside the ASIC. The external logic sequencing circuit requests an intermediate and final energy sample from the external energy ADC. These two values can then be effectively ratioed and discriminated through a look-up logic memory device to determine if the event came from the NaI(Tl) or LSO scintillator. The integrated signals for the NaI(Tl) and LSO is shown in FIG. 15. The deviation from a pure exponential behavior for LSO is caused by the filtering circuitry necessary to cancel the light decay of NaI(Tl) for improved count rate performance.

Figure 16:
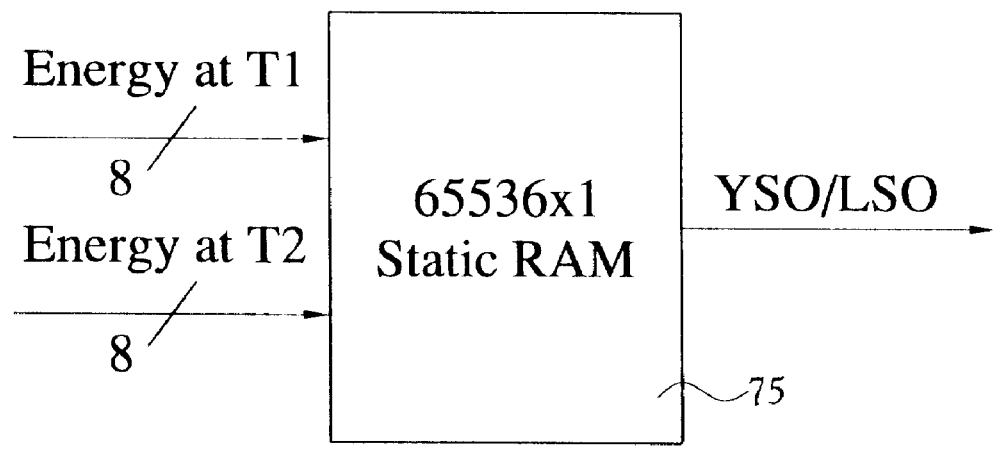
FIG. 16 In the two-sample shape discrimination, the integrated energy signal is sampled using an 8-bit flash converter at approximately 80 ns (E1) and again at 256 ns (E2). The energies (E1) and (E2) are used to determine if the event occurred in a NaI(Tl) or an LSO crystal. The ratios of the energies (E1) and (E2) are used for the shape discrimination. A 65536x1 static RAM can be used to indicate the crystal type as shown in FIG. 16.
Figure 17:
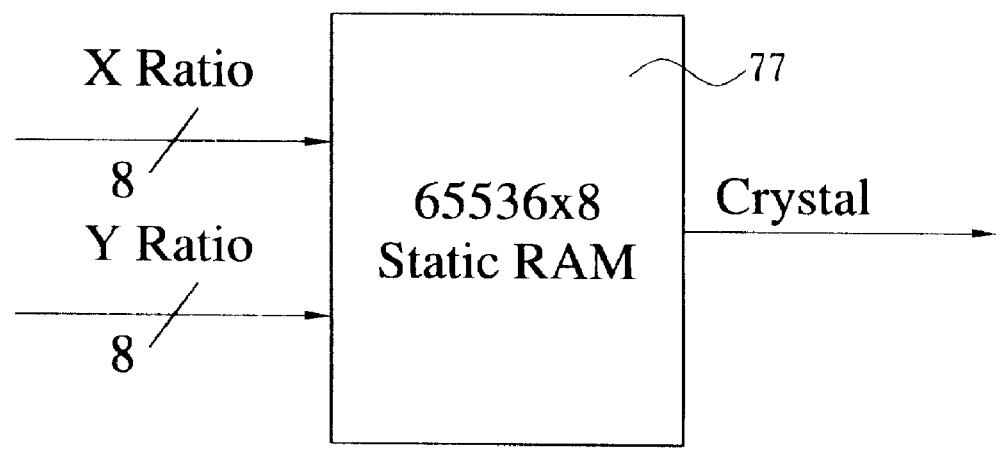
FIG. 17 The integrated X and Y values are digitized at 256 ns using flash converters with the integrated energy signal as the reference to produce the (A+B)/Sum and (A+C)/Sum ratios. The X and Y ratios are used to determine the crystal in which the event occurred. A 65536×8 static RAM can be used to indicate the crystal as shown in FIG. 17.

In order to utilize the two-sample shape discrimination, it is necessary to ensure that the energy integrator is sufficiently linear at the sample points for the NaI(Tl) and LSO scintillation detector signals. The integrated energy signal is sampled using an 8-bit flash converter at approximately 80 ns (El) and again at 256 ns (E2). The energies (E1) and (E2) are used to determine if the event occurred in a NaI(Tl) or an LSO crystal. The ratios of the energies (E1) and (E2) are used for the shape discrimination. A 65536x1 static RAM 75 can be used to indicate the crystal type as shown in FIG. 16. The integrated X and Y values are digitized at 256 ns using flash converters with the integrated energy signal as the reference to produce the (A+B)/Sum and (A+C)/Sum ratios. The X and Y ratios are used to determine the crystal in which the event occurred. A 65536x8 static RAM 77 can be used to indicate the crystal as shown in FIG. 17.

Figure 12:
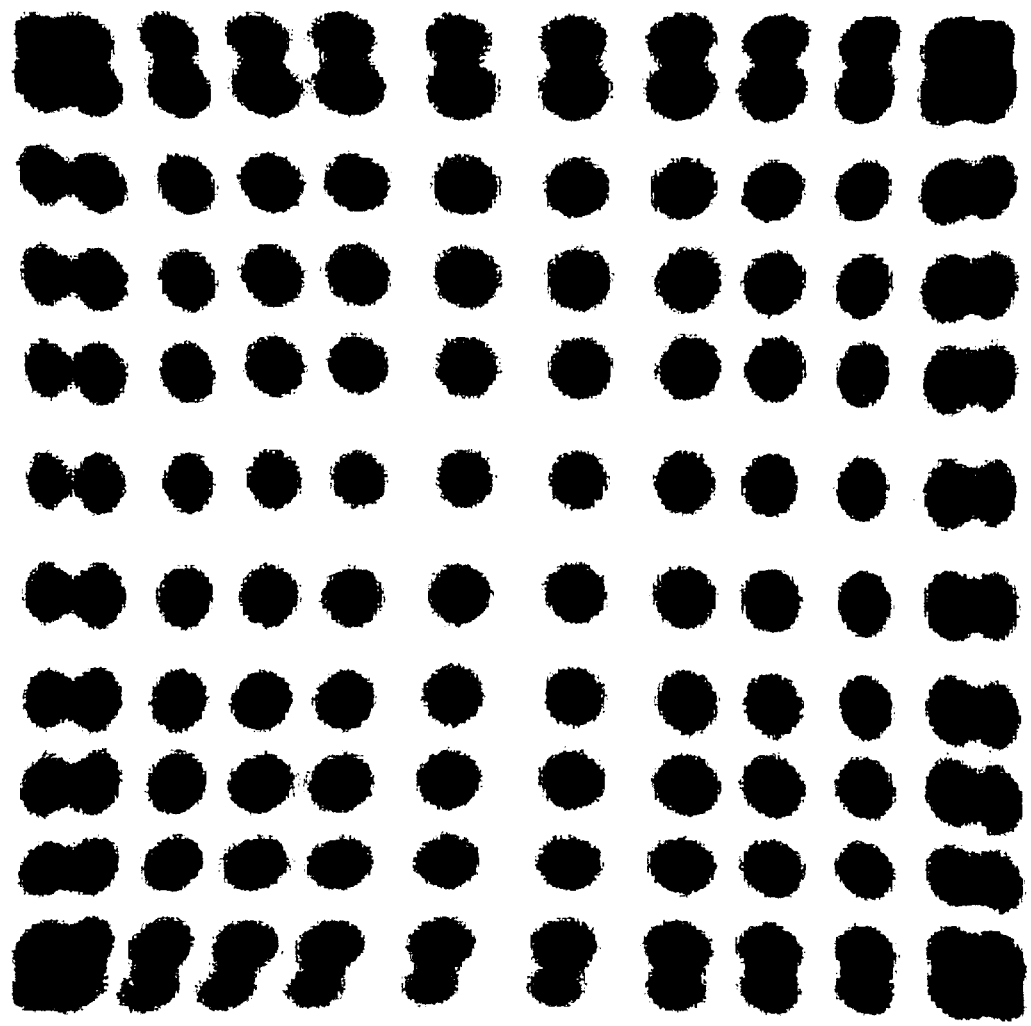
FIG. 12 is the position histogram displaying all 144 discrete NaI(Tl) scintillator elements for the detector design as exhibited in FIG. 3(a). In this case one scintillator layer (slow) is composed of NaI(Tl) and the other scintillator layer (fast) is composed of LSO. The detector is uniformly irradiated with 140 keV gamma-rays from Tc-99 m.
Figure 13:
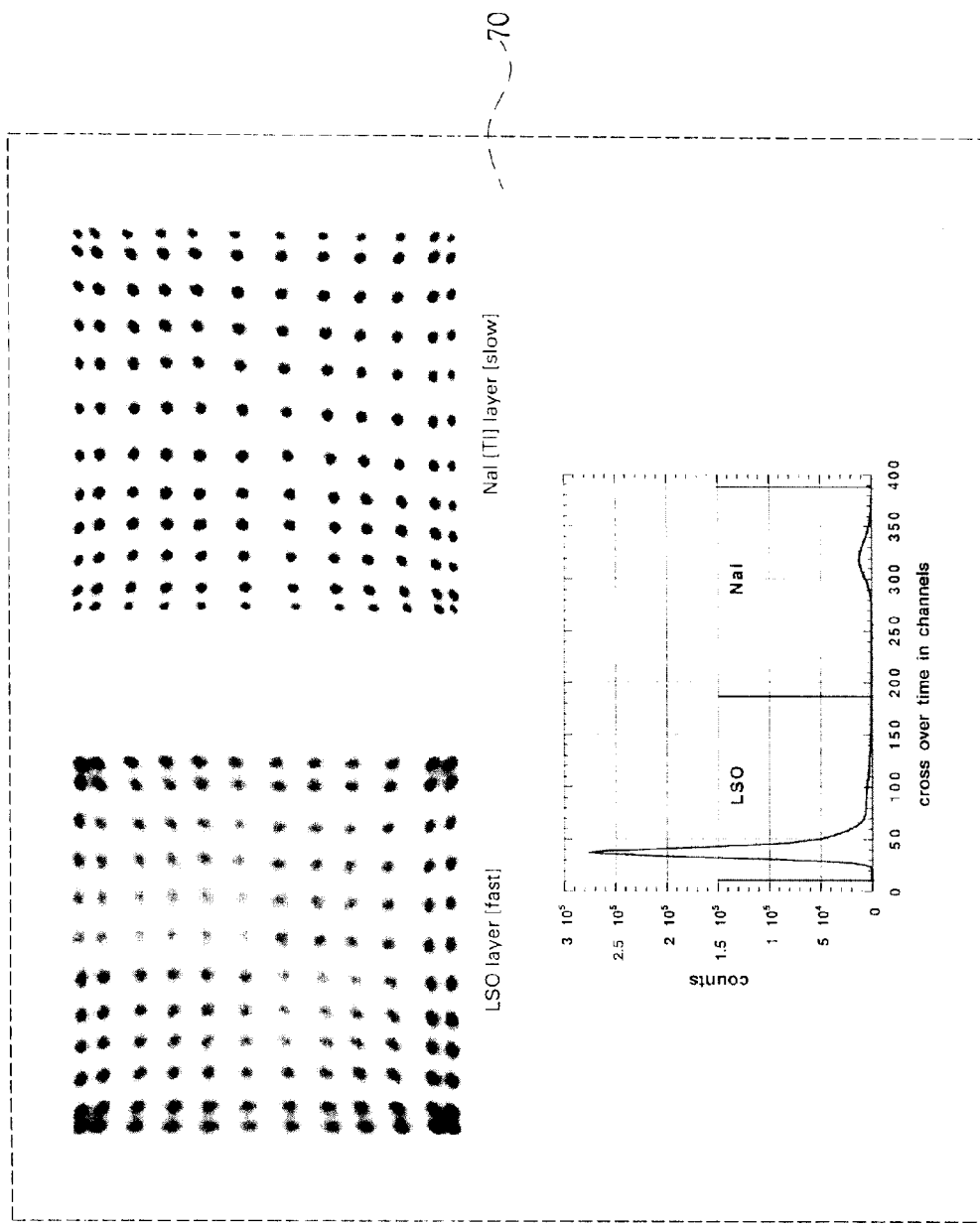
FIG. 13 is the Cross-over time spectra and position histograms for the detector design as exhibited in FIG. 3(a). In this case one scintillator layer (slow) is composed of NaI(Tl) and the other scintillator layer (fast) is composed of LSO. The detector is uniformly irradiated by 511 keV gamma-rays from Ge-68. Pulse Shape Discrimination as provided in FIG. 18. is used to determine in which of the two scintillator layers the gamma-rays interacted. The cross-over time spectra is shown in FIG. 13 for the two scintillator layers. The position histograms are labeled 'slow' for the NaI(Tl) layer and 'fast' for the LSO layer. The position histograms exhibit excellent separation of the 144 discrete elements for each scintillator layer.
Figure 14:
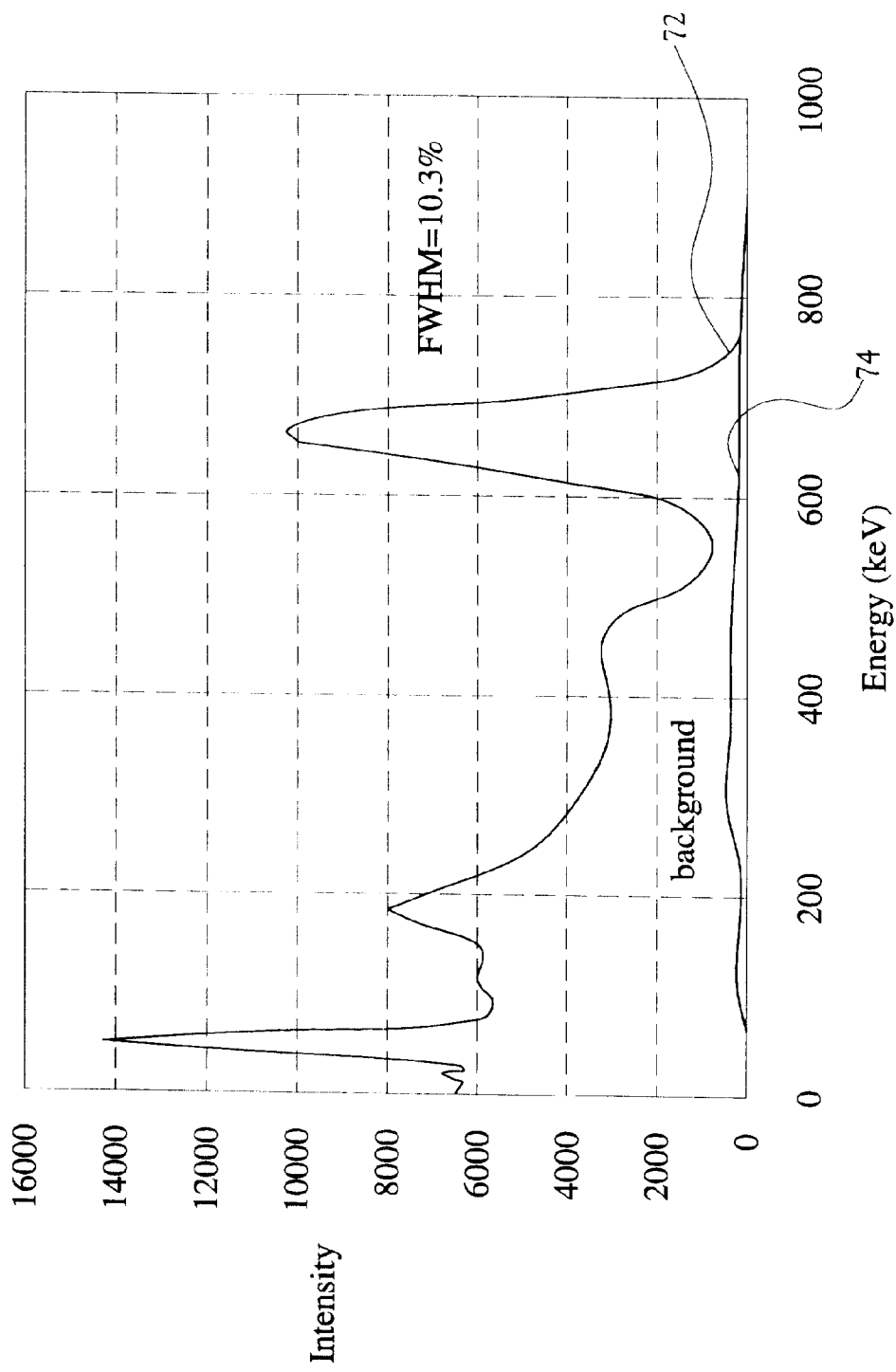
FIG. 14 is a pulse height energy spectrum for an LSO crystal irradiated by 662 keV gamma-rays from Cs-137. Also exhibited in the spectrum is the 2.6% abundant Lu-176 background of LSO.
Figure 18:
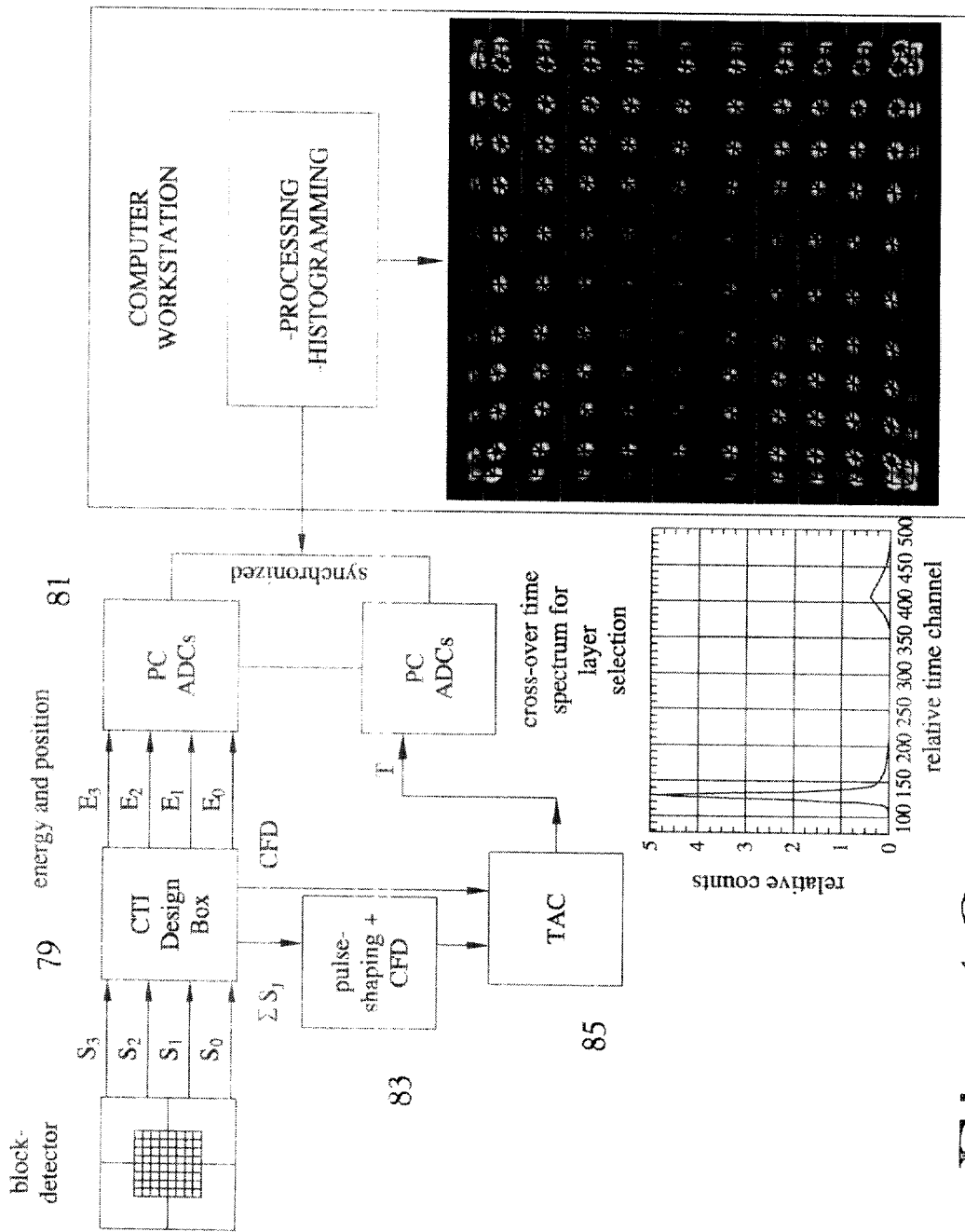
FIG. 18 displays the block diagram of the setup used to evaluate the detectors.

FIG. 18 exhibits the block diagram of the method used to evaluate the prototype detectors for energy, position and time (see FIGS. 12 and 13). The module 79 labeled "CTI Design Box" incorporates a preamp, timing filter amp, sum amp, CFD, and digital clock. The rest of the Figure illustrates standard nuclear spectroscopy instrumentation—such as is available from EG&G Ortec (e.g. 1995 EG&G Ortec catalog "Modular Pulse-Processing Electronics and Semiconductor Radiation Detectors")—processing for performing pulse shape discrimination. For example, those skilled in the art will appreciate that module 81 is a standard personal computer with analog to digital converters, module 83 is for pulse shaping and includes a Constant Fraction Discriminator and that module 85 is a Time-to-Amplitude Converter. Analysis of the two prototype blocks in terms of energy and crystal identification demonstrates that when the devices are operated in the SPECT mode all the individual NaI(Tl) discrete element detectors can be identified at 140 keV. Further, the average pulse height energy resolution at 140 keV is 10.3% for prototype detector block #1 and 10.0% for block #2. The median pulse height energy resolution is below 10.0% in both cases. This performance is comparable to current SPECT imaging systems. When operated in the PET mode, all the individual NaI(Tl) and LSO discrete element detectors are easily identified. The average pulse height energy resolution measured at 511 keV is below 10.1% for both scintillator layers (less than 8.0% for the NaI(Tl) layer). This indicates excellent PET performance comparable to existing PET imaging systems.

Figure 19:
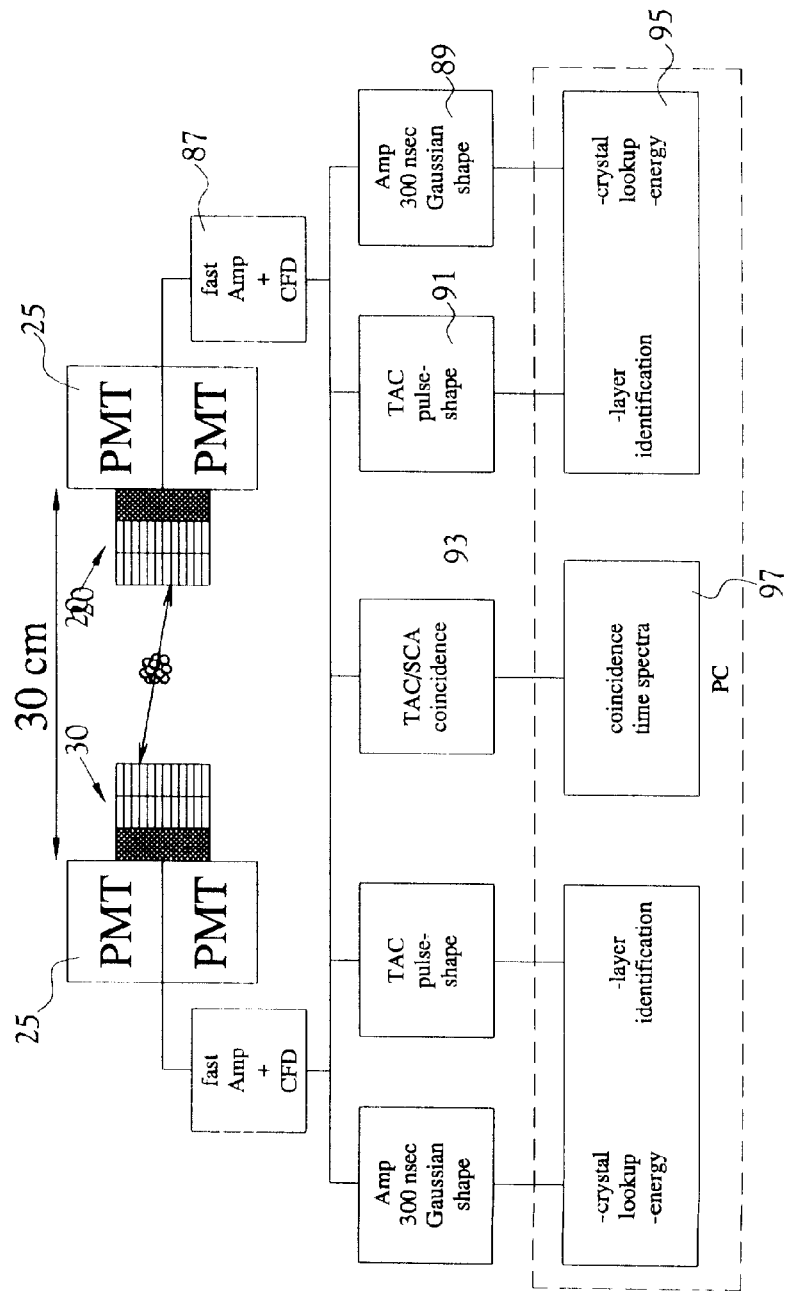
FIG. 19 displays the block diagram for the coincidence setup.
Figure 20:
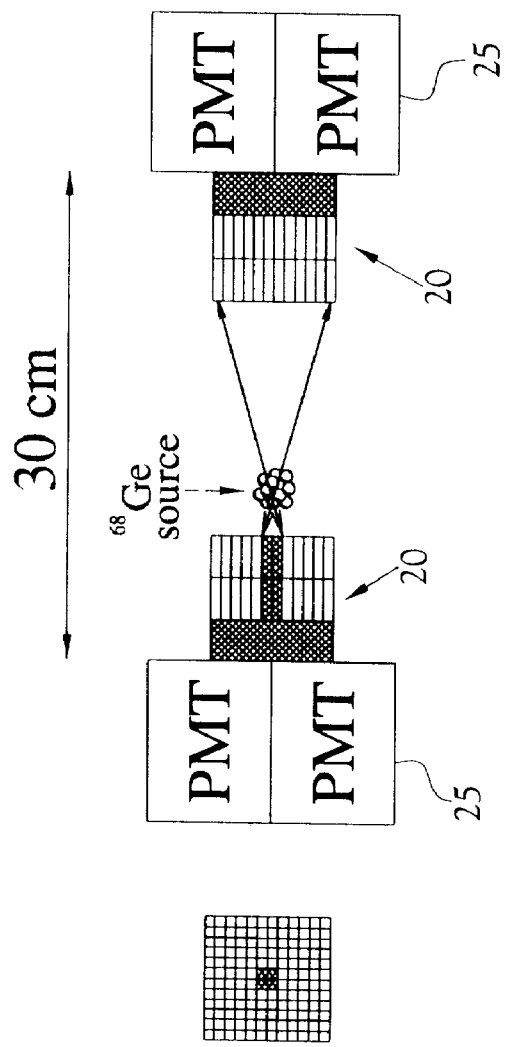
FIG. 20 displays the geometric arrangement used in coincidence timing measurements.
Figure 21:
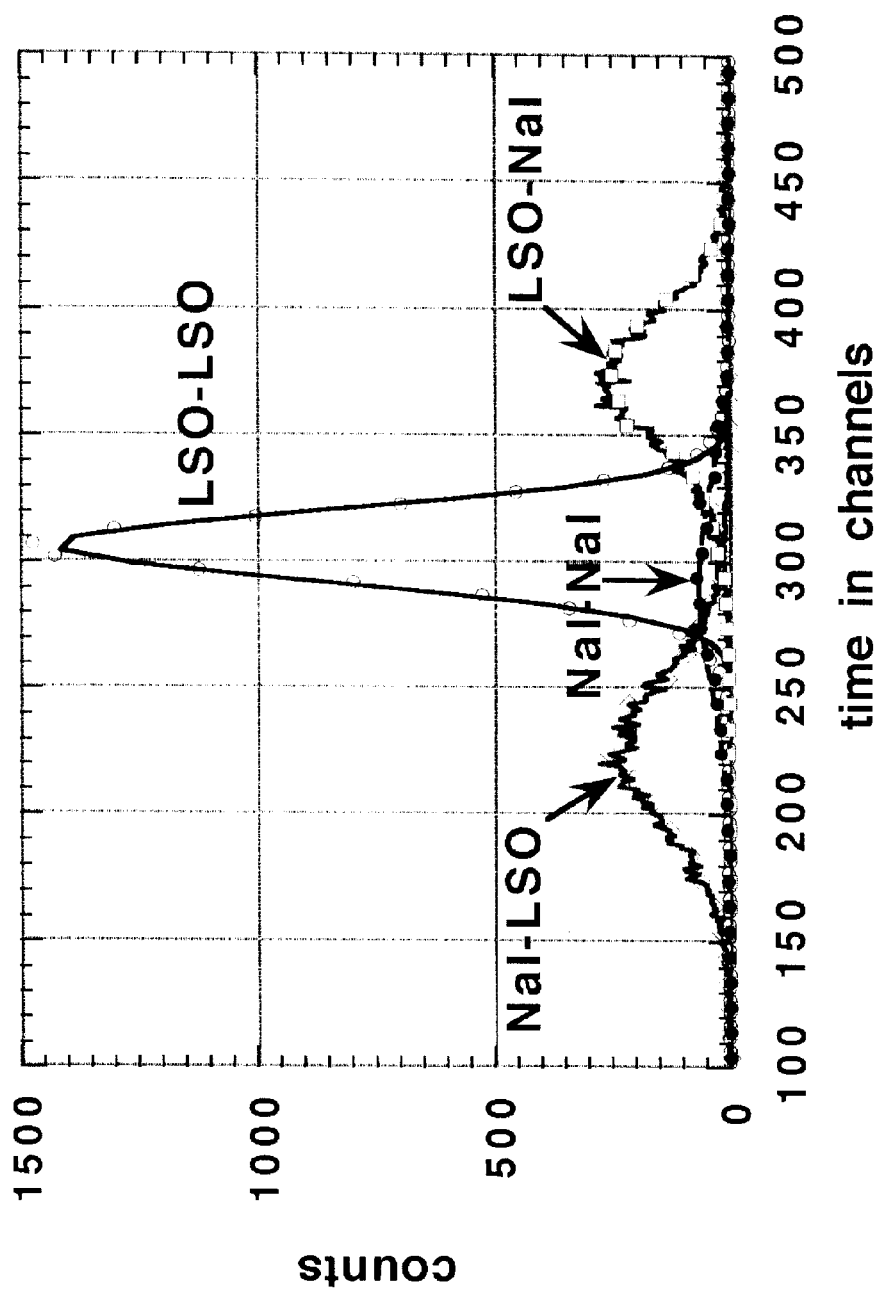
FIG. 21 displays the coincidence time spectra for the various scintillator layer combinations.
Figure 22:
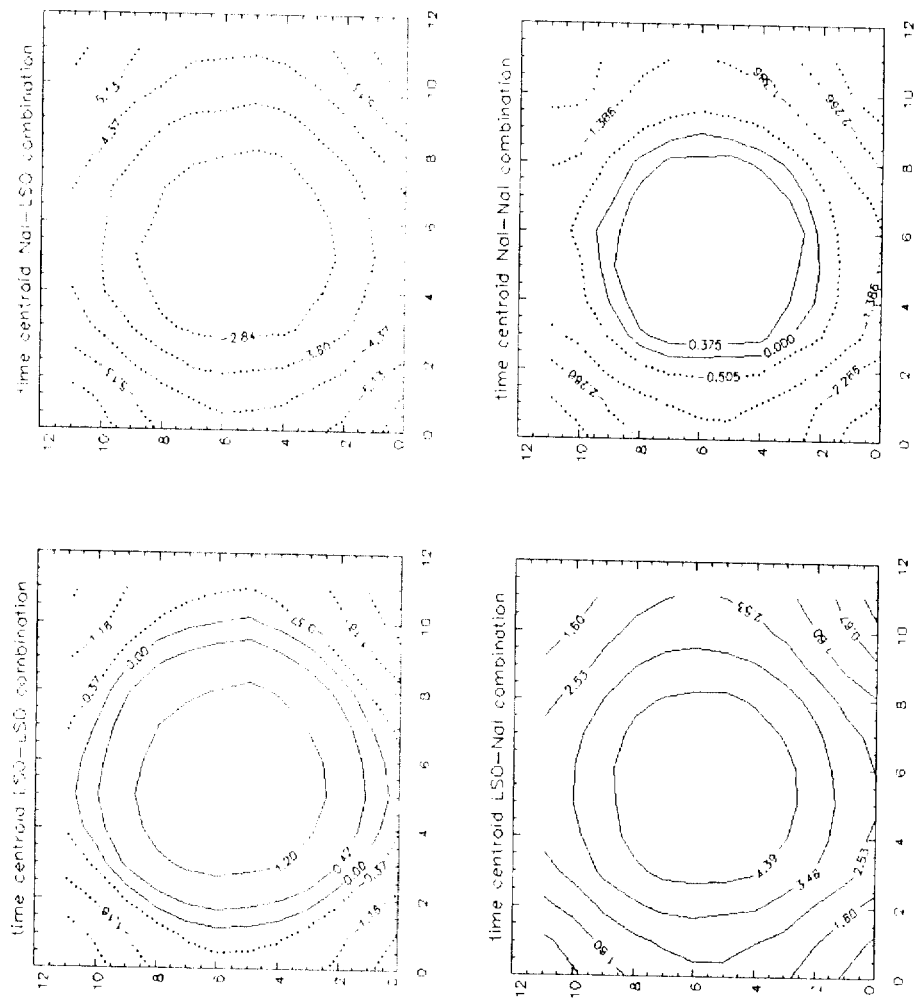
FIG. 22 displays the contour plots for coincidence time centroids in nsec for the various scintillator layer combinations. The zero-line is based on the mean LSO-LSO centroid position. The time centroids are symmetric, but the centroid position is dependent upon the location of the discrete scintillator element with respect to the PMT and reflects the spatial uniformity in the anode output. The time centroid shifts can be corrected via a lookup table.
Figure 23:
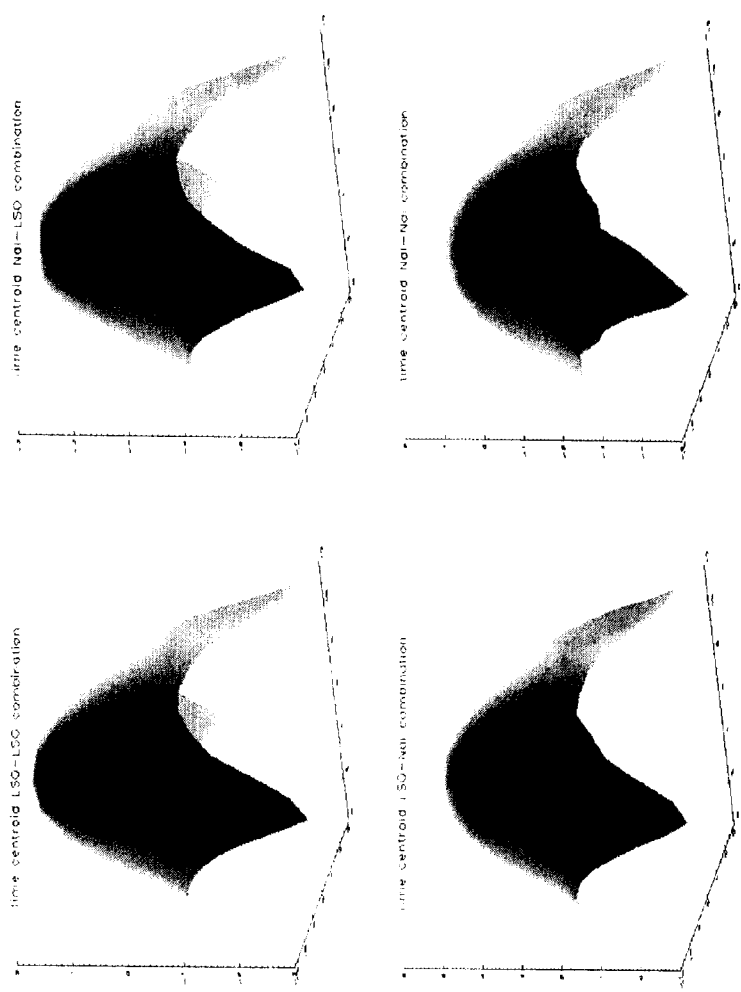
FIG. 23 similarly displays the surface plots for coincidence time centroids in nsec for the various scintillator layer combinations.

FIG. 19 exhibits the block diagram used in the determination of coincidence performance. Similarly FIG. 19 illustrates standard nuclear spectroscopy instrumentation. For example module 87 is a fast shaping amplifier along with a constant fraction discriminator, and module 93 is a time-to-amplitude converter with a single channel analyzer. The output at module 97 is illustrated in FIG. 21. FIG. 20 exhibits the geometric configuration used in measuring the coincidence timing. The figure illustrates 2×2 center crystals for each scintillator layer of the one crystal block is used in coincidence with the 144 crystal elements of each layer of the opposing block. Time spectra are then measured for each of the 144 crystal elements of each scintillator layer. FIG. 21 displays the coincidence time spectra for each layer combination. The time centroids are symmetric, but the centroid position is dependent upon the location of the discrete crystal element with respect to the PMT, and reflects the spatial uniformity in the anode output (see FIGS. 22 & 23). The time centroid shifts can be corrected via a lookup table. Time resolution is scintillator layer combination dependent. The LSO-LSO combination exhibits 1.6 nsec time resolution, indicating PET coincidence timing with 6 nsec time window is feasible.

Figure 24:
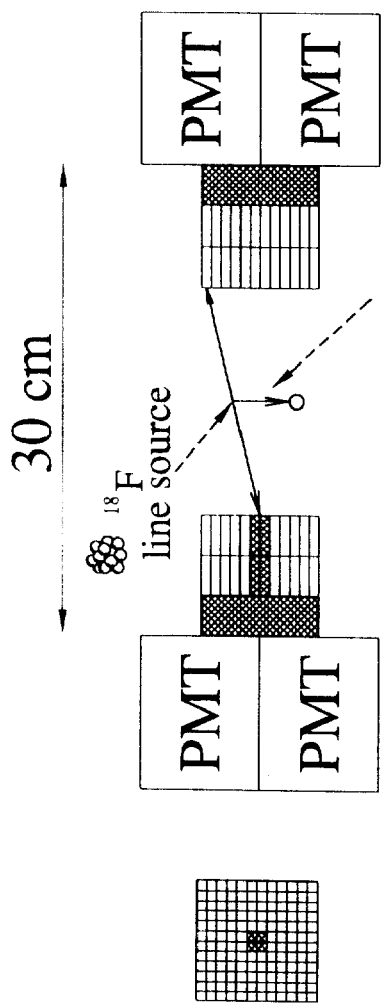
FIG. 24 displays the geometric arrangement used in the line spread function measurements.
Figure 25:
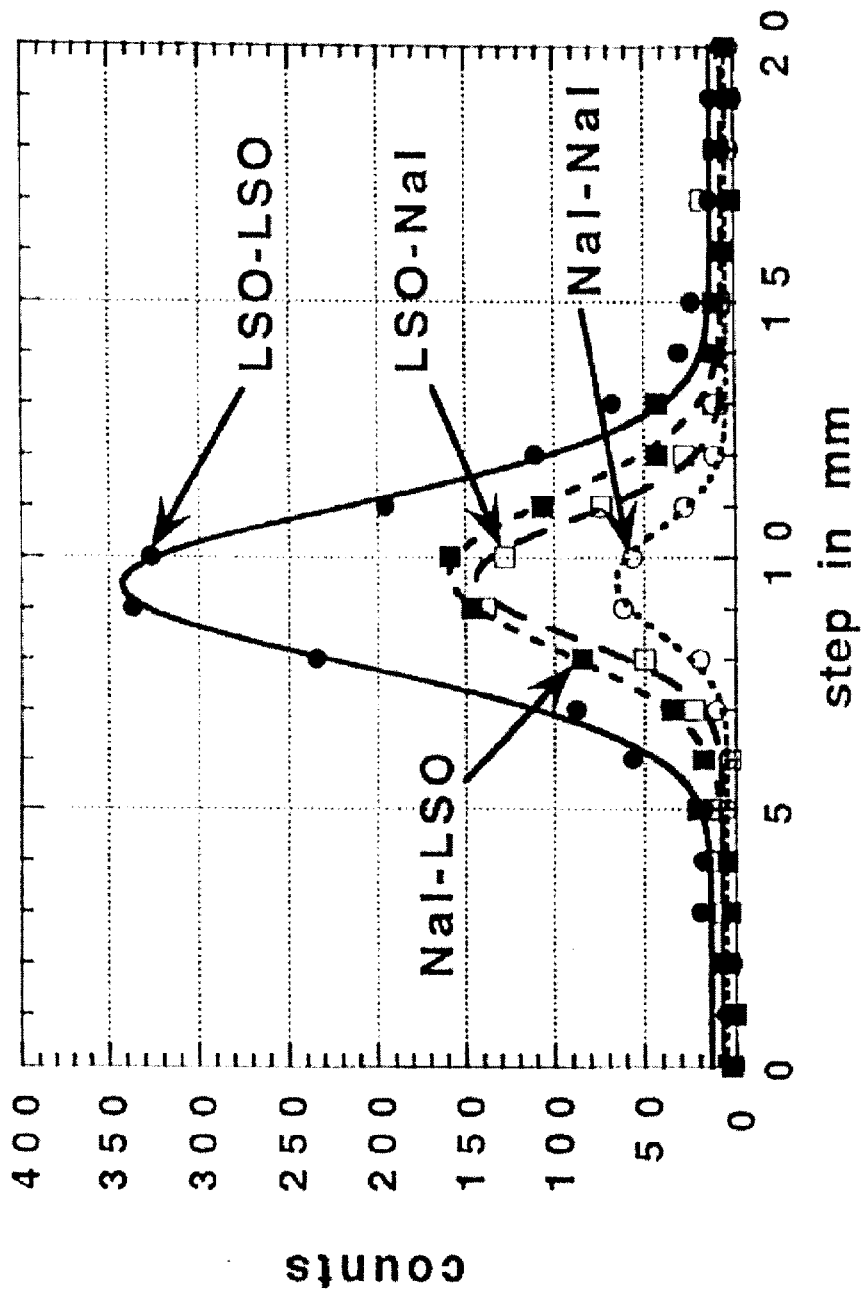
FIG. 25 displays the line spread functions for the various scintillator layer combinations.

The line spread function (LSF) method was used to assess the spatial resolution of the prototype detector blocks. FIG. 24 exhibits the geometric arrangement used in the LSF measurement. FIG. 25 exhibits the step wise data of the LSF for the layer combinations, and Table 2 provides the LSF data in terms of full width at half maximum (FWHM) of the LSF.

TABLE 2

Line spread functions for the layer combinations of the detector design exhibited in FIG. 3(a) where scintillator layer (1) is composed of Nal [T] and scintillator layer (2) ia composed of LSO. The detector is irradiated with 511 keV gamma rays from an F-18 line source. See FIG. (24) for geometric arrangement.

| Combination | FWHM [mm] | StdDev [mm] |
|---|---|---|
| LSO-LSO (back-back) | 3.5 | 0.2 |
| NaI-LSO (front-back) | 3.0 | 0.4 |
| LSO-NaI (front-back) | 3.1 | 0.3 |
| NaI-NaI (front-front) | 2.8 | 0.5 |

The LSF data indicates the depth of interaction (DOI) effects and that a reconstructed spatial resolution of less than 4 mm is possible.

Figure 26:
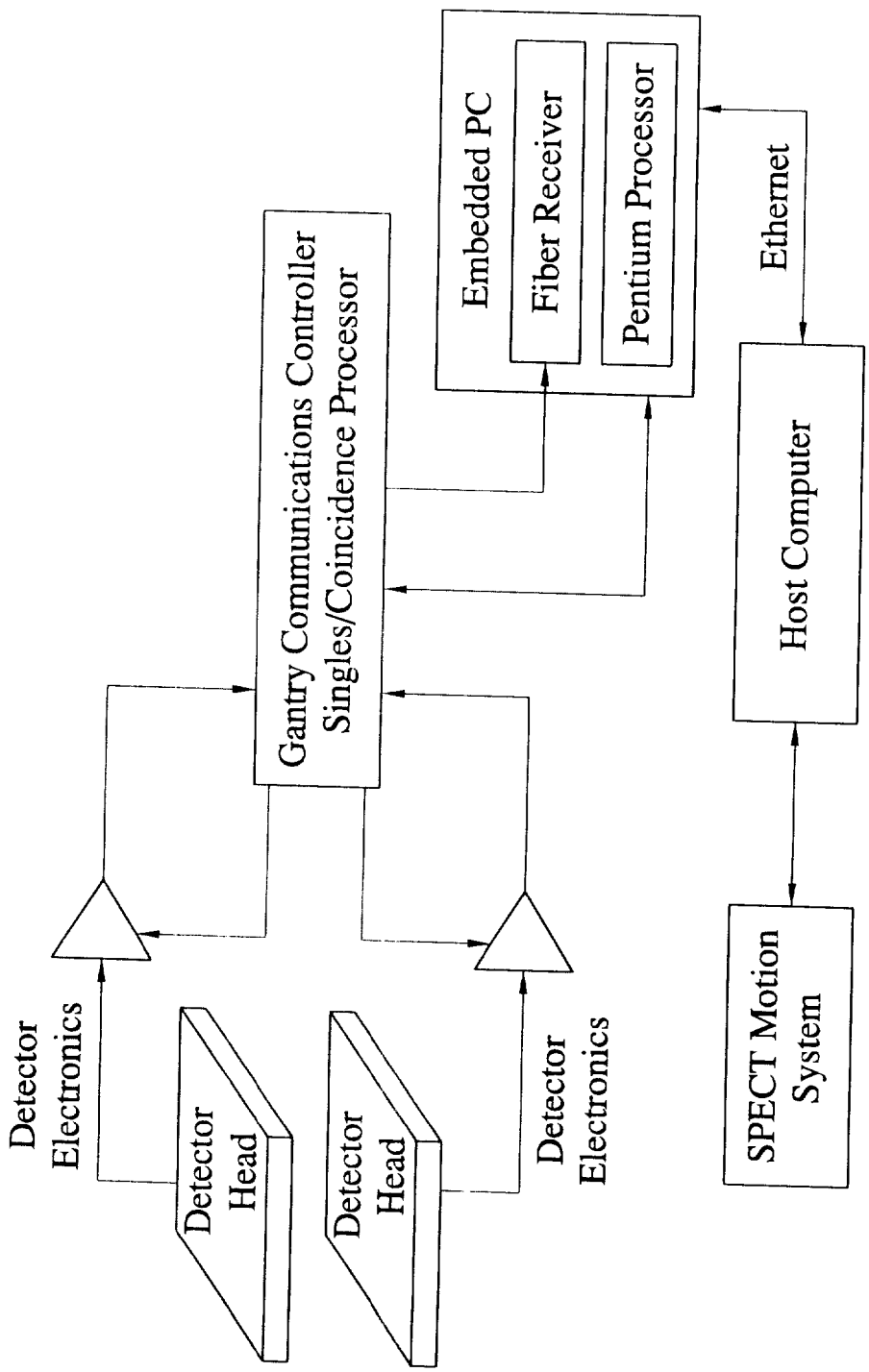
FIG. 26 displays the general system architecture of the medical imaging system.

FIG. 26. displays the general system architecture for application in PET/SPECT medical imaging.

Absolute Sensitivity of Pet/spect

The following calculation was done to predict the absolute sensitivity of the proposed PET/SPECT medical imaging system. Absolute sensitivity is defined as the ratio of the events detected by the system to those emitted from a line source placed at the center of the tomograph. The length of the source is the same as the axial length of the scanner. If the sensitivity of the detector to single events is known then the calculation of absolute sensitivity is the product of the fraction of solid angle and the square of the singles sensitivity.

$$\eta_{Ab}=\eta_{Geom}\cdot\eta^2_{Det}$$

For the NaI/LSO detector, both a Monte Carlo simulation and a measurement were done. These are summarized in the table below:

| Coincidence Sensitivity of NaI/LSO Detector | | | |
|---|---|---|---|
| | Calculated Absolute | Calculated Relative | Measured Relative |
| LSO/LSO | 12.7% | 52.7% | 50.1% |
| LSO/NAI | 4.8% | 19.9% | 20.4% |
| NaI/LSO | 4.8% | 19.9% | 20.4% |
| NaI/NaI | 1.8% | 7.5% | 9.0% |

Total Absolute 24.10%

Assuming two 50 cm transaxial by 40 cm axial detectors, directly opposing and 72 cm face to face, the fraction of the solid angle is found to be 6.2%. Using the total detector sensitivity from table above, the absolute sensitivity is found to be 1.5%.

For whole body scanning, the body is longer than the axial extent of the scanner. Then, if one arbitrarily picks a length for the source of 70 cm, it is possible to put the absolute sensitivity of the scanner in perspective by comparing to existing scanners. The table below compares the PET/SPECT, Siemens ECAT ART, and Siemens ECAT HR+ for both a line source of axial extent and one of 70 cm.

| Absolute Sensitivity Comparison of PET/SPECT | | | |
|---|---|---|---|
| | Axial Length Source | | 70 cm Source |
| | Measured | Calculated | Calculated |
| ART | 1.04% | 1.10% | 0.25% |
| HR+ | 2.94% | 2.80% | 0.62% |
| PET/SPECT | | 1.50% | 0.86% |

Count-rate Performance of Pet/spect

To assess the performance of the PET/SPECT in an imaging situation, the proposed machine was compared to an existing Siemens ECAT ART tomograph. Since the count-rate performance of the machine is a function of the detector singles rate, this needs to be known along with the trues sensitivity. The randoms rate can be computed from the singles rates and the coincidence window.

A typical whole-body study performed on an ART was used as a bench mark. The study consisted of five bed steps ranging from the patients nose to just above the bladder. The variation in the count-rate with respect to bed step was minimal. Due to this, the rates were averaged to give the following results:

| ART Whole-body Study 5mCi Injection | |
|---|---|
| Trues | 20666 cps |
| Randoms | 10166 cps |
| Singles/Block | 27716 cps |

The singles sensitivity of the ART blocks and dead-time are obtained by fitting the singles rates obtained in a count-rate study done with a 20 cm uniform phantom filled with $^{18}$F. To model the response of the system to the subject, the trues were set so that for the singles rate of the subject study, the trues also matched. The randoms were calculated from the singles and the coincidence window. The dead-time is based on the fitted dead-time function. This process lets the performance of the system be modeled with respect to activity. The NEC rate shown in the right most column did not include a scatter term and was simply $T^2/(T+2 \cdot R)$.

For PET/SPECT, results were used from the Monte Carlo model of absolute sensitivity to obtain ratios for the singles and trues sensitivity. These values are given in the table below:

| PET /SPECT Sensitivity (cps/uCi/cc) | |
|---|---|
| Trues Sensitivity | 816000 |
| Singles/Block/Sensitivity | 175000 |

The dead-time of the system is modeled based on the electronic dead-time of 320 nS and the following relation:

$$S_{Observed} = S_{Incident} \cdot \frac{\exp(-8 \cdot S_{Incident} \cdot \tau_{dead})}{(1 + S_{Incident} \cdot \tau_{dead})}$$

This relation takes into account the overlapped detector structure that forces eight surrounding detectors to be dead during the processing of an event in one detector.

With these values, it is possible to predict the performance of the system to different injection levels as shown in the following chart:

| | Whole-body Imaging Performance of PET/SPECT | | | | | | | | | |
|---|---|---|---|---|---|---|---|---|---|---|
| | ART | | | | | PET/SPECT 40 cm fov, 320 ns Deadtime | | | | |
| Activity[1] | Singles cps | Livetime | Trues cps | Randoms cps | NEC cps | Singles cps | Livetime | Trues cps | Randoms cps | NEC cps |
| 0.500 | 89286 | 36.3% | 41550 | 87111 | 8001 | 37304 | 18.2% | 74157.6 | 53437 | 30378 |
| 0.475 | 86210 | 38.0% | 41306 | 82270 | 8289 | 36975 | 19.8% | 76690.0 | 52499 | 32371 |
| 0.450 | 83031 | 39.8% | 40967 | 77300 | 8582 | 36548 | 21.5% | 79092.1 | 51294 | 34432 |
| 0.425 | 79742 | 41.6% | 40524 | 72215 | 8879 | 36015 | 23.4% | 81320.9 | 49809 | 36549 |
| 0.400 | 76338 | 43.6% | 39965 | 67030 | 9178 | 35368 | 25.5% | 83326.4 | 48035 | 38704 |
| 0.375 | 72814 | 45.7% | 39279 | 61762 | 9477 | 34598 | 27.8% | 85051.1 | 45965 | 40873 |
| 0.350 | 69163 | 48.0% | 38452 | 56431 | 9771 | 33694 | 30.3% | 86429.1 | 43596 | 43625 |
| 0.325 | 65379 | 50.3% | 37470 | 51063 | 10058 | 32648 | 33.0% | 87384.9 | 40930 | 45119 |
| 0.300 | 61455 | 52.9% | 36317 | 45685 | 10330 | 31447 | 35.9% | 87831.9 | 37974 | 47102 |
| 0.275 | 57383 | 55.5% | 34975 | 40330 | 10579 | 30081 | 39.1% | 87671.7 | 34746 | 48906 |
| 0.250 | 53155 | 58.4% | 33424 | 35038 | 10794 | 28537 | 42.5% | 86792.2 | 31271 | 50443 |
| 0.225 | 48762 | 61.4% | 31642 | 29852 | 10961 | 26802 | 46.3% | 85065.7 | 27584 | 51601 |
| 0.200 | 44195 | 64.6% | 29604 | 24826 | 11058 | 24862 | 50.5% | 82347.7 | 23736 | 52235 |

-continued

Whole-body Imaging Performance of PET/SPECT

| | ART | | | | | PET/SPECT 40 cm fov, 320 ns Deadtime | | | | |
|---|---|---|---|---|---|---|---|---|---|---|
| Activity[1] | Singles cps | Livetime | Trues cps | Randoms cps | NEC cps | Singles cps | Livetime | Trues cps | Randoms cps | NEC cps |
| 0.175 | 39445 | 68.1% | 27283 | 20020 | 11056 | 22703 | 55.0% | 78474.3 | 19792 | 52163 |
| 0.150 | 34499 | 71.8% | 24647 | 15502 | 10916 | 20308 | 59.9% | 73260.0 | 15837 | 51147 |
| 0.125 | 29347 | 75.7% | 21664 | 11355 | 10577 | 17662 | 65.2% | 66495.2 | 11979 | 48883 |
| 0.100 | 23975 | 79.9% | 18294 | 7671 | 9950 | 14747 | 71.0% | 57943.4 | 8351 | 44979 |
| 0.075 | 18370 | 84.4% | 14494 | 4558 | 8898 | 11543 | 77.3% | 47337.8 | 5117 | 38923 |
| 0.050 | 12517 | 89.2% | 10216 | 2142 | 7198 | 8032 | 84.3% | 34377.8 | 2477 | 30047 |
| 0.025 | 6406 | 94.4% | 5405 | 567 | 4468 | 4192 | 91.8% | 18725.3 | 675 | 17467 |
| 0.000 | 0 | 100.0% | 0 | 0 | 0 | 0 | 100.0% | 0 | 0 | 0 |

[1]arbitrary units
Based on WB scan on Hannover ART with ~5
mCi injection (Activity = .11 arbitrary units)
Exact with septa has NEC of 17500 for 10 mCi injection.
ART Coincidence Sensitivity: 229000 cps/$\mu$Ci/cc
PET/SPECT Coincidence Sensitivity: 816000 cps/$\mu$Ci/cc
NEC does not include a scatter term for either scanner From the foregoing description, it will be recognized by those skilled in the art that a detector array, having particular application in Single Photon Imaging which includes traditional Gamma Cameras, Planar Imaging, Single Photon Emission Computed Tomography (SPECT) with or without Coincidence Photon Imaging and Positron Emission Tomography (PET), offering advantages over the prior art has been described and shown. Specifically, the detector array of the present invention incorporates either a single scintillator layer or two, stacked discrete scintillator layers that can be the same scintillator material or of two different scintillator materials. In either case the different layers are composed of materials that have distinctly different decay times. The variants in these figures are the types of optical detectors which are used, i.e. photomultipliers and/or photodiodes. Additionally, the optical light guide can be integral with the scintillators or optically bonded thereto. Further, the light guide can be active or non-active. In either of these variants, the light guide can be segmented or non-segmented. And, if segmented, can either be inverted or non-inverted.

While a preferred embodiment has been shown and described, it will be understood that it is not intended to limit the disclosure, but rather it is intended to cover all modifications and alternate methods falling within the spirit and the scope of the invention as defined in the appended claims.

Having thus described the aforementioned invention, We claim:

1. A scintillation detector array for encoding energy, position and time coordinates of gamma ray interactions for use in Single Photon Emission Tomography, Single Photon Emission Tomography with coincidence photon imaging, Planar Imaging, and Positron Emission Tomography imaging, said scintillation detector array comprising:

a plurality of discrete scintillator elements which interact with incident gamma-rays to produce a quantifiable number of scintillation photons;

an optical detector associated with each of said plurality of discrete scintillator elements and positioned for sensing and quantifying said scintillation photons exiting each of said plurality of discrete scintillator elements;

a segmented light guide disposed between said plurality of discrete scintillator elements and said associated optical detectors, said segmented light guide having a plurality of optical barriers of predetermined lengths to control the distribution of scintillation photons along the axial and transaxial dimensions of said segmented light guide for scintillation photons exiting said discrete scintillators;

a means operatively associated with said scintillation detector array for determining time, energy and transverse and longitudinal position coordinates of gamma ray interactions in said plurality of discrete scintillator elements.

2. The scintillation detector array of claim 1 wherein said plurality discrete scintillator elements define a block, wherein a plurality of blocks defined an array of scintillator blocks and said plurality of optical detectors define an array of optical detectors positioned adjacent said array of blocks, each of said plurality of scintillator blocks being adjacent one quadrant of each of four of said plurality of adjacent optical detectors.

3. The scintillation detector array of claim 1 wherein said plurality discrete scintillator elements, which interact with incident gamma-rays to produce a quantifiable number of scintillation photons, are arranged in an (m)×(n) array, and said plurality of optical detectors are arranged in an (q)×(p) array, wherein said plurality of optical detectors is for sensing and quantifying said scintillation photons exiting each of said plurality of discrete scintillator elements.

4. The scintillator detector array of claim 3 wherein said (m)×(n) array equals said (q)×(p) array.

5. The scintillator detector array of claim 3 wherein said (m)×(n) array does not equal said (q)×(p) array.

6. The scintillation detector array of claim 1 wherein said segmented light guide is inverted.

7. The scintillation detector array of claim 1 wherein said segmented light guide is non-inverted.

8. The scintillation detector array of claim 1 wherein said segmented light guide is active such that the light guide is integral with said plurality of discrete scintillator elements.

9. The scintillation detector array of claim 1 wherein said scintillator defines a first and second layer, said first layer being composed of a first selected scintillator material and said second layer being composed of a second selected scintillator material, wherein said first layer has a first selected decay time and said second layer has a second selected decay time, wherein said first selected decay time is not equal to said second selected decay time and wherein said first and second selected scintillator materials are stacked one upon the other, whereby a pulse shape discrimination technique is used to determine which said layer the gamma ray interacts.

10. The scintillation detector array of claim 1 wherein said scintillator defines a first and second layer, said first layer being composed of a first selected scintillator material and said second layer being composed of a second selected scintillator material and wherein said first and second selected scintillator materials are stacked one upon the other, whereby a pulse height discrimination technique is used to determine which said layer the gamma ray interacts.

11. A scintillation detector array for encoding energy, position and time coordinates of gamma ray interactions for use in Single Photon Emission Tomography, Single Photon Emission Tomography with coincidence photon imaging, Planar Imaging, and Positron Emission Tomography imaging, said scintillation detector array comprising:
a plurality of discrete scintillator elements which interact with incident gamma-rays to produce a quantifiable number of scintillation photons, wherein each of said plurality of discrete scintillators is composed of a first layer having a first selected decay time and a second layer having a second selected decay time, wherein said first selected decay time is not equal to said second selected decay time;
an optical detector associated with each of said plurality of discrete scintillator elements and positioned for sensing and quantifying said scintillation photons exiting each of said plurality of discrete scintillator elements;
an inverted segmented light guide disposed between said plurality of discrete scintillator elements and said associated optical detectors, said inverted segmented light guide having a plurality of optical barriers of predetermined lengths to control the distribution of scintillation photons along the axial and transaxial dimensions of said inverted segmented light guide for scintillation photons exiting said discrete scintillators;
a means operatively associated with said scintillation detector array for determining time, energy and transverse and longitudinal position coordinates of gamma ray interactions in said plurality of discrete scintillator elements.

12. The scintillation detector array of claim 11 wherein said plurality discrete scintillator elements define a block, wherein a plurality of blocks define an array of scintillator blocks and said plurality of optical detectors define an array of optical detectors positioned adjacent said array of blocks, each of said plurality of scintillator blocks being adjacent one quadrant of each of four of said plurality of adjacent optical detectors.

13. The scintillation detector array of claim 11 wherein said plurality discrete scintillator elements, which interact with incident gamma-rays to produce a quantifiable number of scintillation photons, are arranged in an (m)×(n) array, and said plurality of optical detectors are arranged in blocks defining an (q)×(p) array, wherein said plurality of optical detectors is for sensing and quantifying said scintillation photons exiting each of said plurality of discrete scintillator elements.

14. The scintillator detector array of claim 13 wherein said (m)×(n) array equals said (q)×(p) array.

15. The scintillator detector array of claim 13 wherein said (m)×(n) array does not equal said (q)×(p) array.

16. The scintillation detector array of claim 13 wherein said scintillation detector array is used for a technique selected from a group consisting of PET imaging and simultaneous PET and SPECT.

17. The scintillation detector array of claim 13 wherein said second scintillator layer defines an active shield against background radiation and wherein a pulse shape discrimination technique is used to reject background events thereby preventing the background events from being counted as singles events in single photon imaging techniques.

18. The scintillation detector array of claim 13 wherein said plurality of optical barriers are defined by grooves of selected depths, and wherein said grooves are filled with silicon dioxide.

19. The scintillation detector array of claim 11 wherein said plurality of optical barriers are defined by grooves of selected depths, and wherein said grooves are filled with a reflector selected from a group consisting of silicon dioxide, titanium dioxide, aluminum oxide, magnesium oxide, barium sulfate, zinc oxide and Teflon powder.

20. The scintillation detector array of claim 11 wherein said first and said second layer of each of said plurality of discrete scintillator elements is composed of Cerium-doped Lutetium Oxyorthosilicate.

21. The scintillation detector array of claim 20 wherein said Cerium-doped Lutetium Oxyorthosilicate is selected for use in techniques for distinguishing pulse heights of gamma ray interactions.

22. The scintillation detector array of claim 11 wherein said first and said second layer of each of said plurality of discrete scintillator elements is composed of Thallium-doped Sodium Iodide.

23. The scintillation detector array of claim 22 wherein said Thallium-doped Sodium Iodide is selected for use in techniques for distinguishing pulse heights of gamma ray interactions.

24. The scintillation detector array of claim 11 wherein said first layer is composed of a first selected scintillator material and said second layer is composed of a second selected scintillator material.

25. The scintillator detector array of claim 24 wherein said first and second selected scintillator materials are stacked one upon the other, whereby a pulse shape discrimination technique is used to determine which said layer the gamma ray interacts.

26. The scintillation detector array of claim 24 wherein said first selected scintillator material and said second selected scintillator material are selected for use in techniques for separating low and high energies.

27. The scintillation detector array of claim 24 wherein said first selected scintillator material and said second selected scintillator material are selected for use in techniques for determining depth of interaction of the gamma rays with said plurality of discrete scintillator elements.

28. The scintillation detector array of claim 24 wherein said first selected scintillator material and said second selected scintillator material are selected for use in techniques for distinguishing neutron interactions from gamma ray interactions with said plurality of discrete scintillator elements.

29. The scintillation detector array of claim 24 wherein said first selected scintillator material and said second selected scintillator material are selected for use in techniques for distinguishing pulse heights of gamma ray interactions.

30. The scintillation detector array of claim 24 wherein said first selected scintillator material is Thallium-doped Sodium Iodide and said second selected scintillator material is a High-Z scintillator material.

31. The scintillation detector array of claim 24 wherein said first selected scintillator material is Cerium-doped Yttrium Oxyorthosilicate and said second selected scintillator material is a High-Z scintillator material.

32. The scintillation detector array of claim 27 wherein said first and said second selected scintillator materials are High-Z scintillator materials.

33. The scintillation detector array of claim 24 wherein said first selected scintillator material is Cerium-doped Lutetium Oxyorthosilicate and said second selected scintillator material is Cerium-doped Gadolinium Oxyorthosilicate.

34. The scintillation detector array of claim 24 wherein said first selected scintillator material is composed of Thallium-doped Sodium Iodide and said second selected scintillator material is Cerium-doped Lutetium Oxyorthosilicate.

35. The scintillation detector array of claim 34 wherein said Thallium-doped Sodium Iodide layer is disposed proximate a subject side and said Cerium-doped Lutetium Oxyorthosilicate layer is optically bonded to said inverted segmented light guide.

36. The scintillation detector array of claim 34 wherein said Cerium-doped Lutetium Oxyorthosilicate layer is chemically etched to optical transparency with pyrophosphoric acid.

37. The scintillation detector array of claim 34 wherein said Cerium-doped Lutetium Oxyorthosilicate is mechanically polished to optical transparency.

38. The scintillation detector array of claim 35 wherein said first selected scintillator material is Cerium-doped Yttrium Oxyorthosilicate and said second selected scintillation material is Cerium-doped Lutetium Oxyorthosilicate.

39. The scintillation detector array of claim 38 wherein said Cerium-doped Yttrium Oxyorthosilicate layer is disposed proximate a subject side and said Cerium-doped Lutetium Oxyorthosilicate layer is optically bonded to said inverted segmented light guide.

40. The scintillation detector array of claim 38 wherein said Cerium-doped Lutetium Oxyorthosilicate layer and said Cerium-doped Yttrium Oxyorthosilicate layer are chemically etched to optical transparency using pyrophosphoric acid.

41. The scintillation detector array of claim 38 wherein said Cerium-doped Lutetium Oxyorthosilicate layer and said Cerium-doped Yttrium Oxyorthosilicate layer are mechanically polished to optical transparency.

42. A scintillation detector array for encoding energy, position and time coordinates of gamma ray interactions for use in Single Photon Emission Tomography, Single Photon Emission Tomography with coincidence photon imaging, Planar Imaging, and Positron Emission Tomography imaging, said scintillation detector array comprising:

a plurality of discrete scintillator elements which interact with incident gamma-rays to produce a quantifiable number of scintillation photons, wherein each of said plurality of discrete scintillators is composed of a first layer having a first selected decay time and a second layer having a second selected decay time, wherein said first selected decay time is not equal to said second selected decay time;

an optical detector associated with each of said plurality of discrete scintillator elements and positioned for sensing and quantifying said scintillation photons exiting each of said plurality of discrete scintillator elements;

a non-inverted segmented light guide disposed between said plurality of discrete scintillator elements and said associated optical detectors, said non-inverted segmented light guide having a plurality of optical barriers of predetermined lengths to control the distribution of scintillation photons along the axial and transaxial dimensions of said non-inverted segmented light guide for scintillation photons exiting said discrete scintillators;

a means operatively associated with said scintillation detector array for determining time, energy and transverse and longitudinal position coordinates of gamma ray interactions in said plurality of discrete scintillator elements.

43. The scintillation detector array of claim 42 wherein said plurality discrete scintillator elements define a block, wherein a plurality of blocks define an array of scintillator blocks and said plurality of optical detectors define an array of optical detectors positioned adjacent said array of blocks, each of said plurality of scintillator blocks being adjacent one quadrant of each of four of said plurality of adjacent optical detectors.

44. The scintillation detector array of claim 42 wherein said plurality discrete scintillator elements, which interact with incident gamma-rays to produce a quantifiable number of scintillation photons, are arranged in an (m)×(n) array, and said plurality of optical detectors are arranged in an (q)×(p) array, wherein said plurality of optical detectors is for sensing and quantifying said scintillation photons exiting each of said plurality of discrete scintillator elements.

45. The scintillator detector array of claim 44 wherein said (m)×(n) array equals said (q)×(p) array.

46. The scintillator detector array of claim 44 wherein said (m)×(n) array does not equal said (q)×(p) array.

47. The scintillation detector array of claim 42 wherein said scintillation detector array is used for a technique selected from a group consisting of PET imaging and simultaneous PET and SPECT.

48. The scintillation detector array of claim 42 wherein said second scintillator layer defines an active shield against background radiation and wherein a pulse shape discrimination technique is used to reject background events thereby preventing the background events from being counted as singles events in single photon imaging techniques.

49. The scintillation detector array of claim 42 wherein said plurality of optical barriers are defined by grooves of selected depths, and wherein said grooves are filled with silicon dioxide.

50. The scintillation detector array of claim 42 wherein said plurality of optical barriers are defined by grooves of selected depths, and wherein said grooves are filled with a reflector selected from a group consisting of silicon dioxide, titanium dioxide, aluminum oxide, magnesium oxide, barium sulfate, zinc oxide and teflon powder.

51. The scintillation detector array of claim 42 wherein said first and said second layer of each of said plurality of discrete scintillator elements is composed of Cerium-doped Lutetium Oxyorthosilicate.

52. The scintillation detector array of claim 51 wherein said Cerium-doped Lutetium Oxyorthosilicate is selected for use in techniques for distinguishing pulse heights of gamma ray interactions.

53. The scintillation detector array of claim 42 wherein said first and said second layer of each of said plurality of discrete scintillator elements is composed of Thallium-doped Sodium Iodide.

54. The scintillation detector array of claim 53 wherein said Thallium-doped Sodium Iodide is selected for use in techniques for distinguishing pulse heights of gamma ray interactions.

55. The scintillation detector array of claim 42 wherein said first layer is composed of a first selected scintillator material and said second layer is composed of a second selected scintillator material.

56. The scintillator detector array of claim 55 wherein said first and second selected scintillator materials are stacked one upon the other, whereby a pulse shape discrimination technique is used to determine which said layer the gamma ray interacts.

57. The scintillation detector array of claim 55 wherein said first selected scintillator material and said second selected scintillator material are selected for use in techniques for separating low and high energies.

58. The scintillation detector array of claim 55 wherein said first selected scintillator material and said second selected scintillator material are selected for use in techniques for determining depth of interaction of the gamma rays with said plurality of discrete scintillator elements.

59. The scintillation detector array of claim 55 wherein said first selected scintillator material and said second selected scintillator material are selected for use in techniques for distinguishing neutron interactions from gamma ray interactions with said plurality of discrete scintillator elements.

60. The scintillation detector array of claim 55 wherein said first selected scintillator material and said second selected scintillator material are selected for use in techniques for distinguishing pulse heights of gamma ray interactions.

61. The scintillation detector array of claim 55 wherein said first selected scintillator material is Thallium-doped Sodium Iodide and said second selected scintillator material is a High-Z scintillator material.

62. The scintillation detector array of claim 55 wherein said first selected scintillator material is Cerium-doped Yttrium Oxyorthosilicate and said second selected scintillator material is a High-Z scintillator material.

63. The scintillation detector array of claim 55 wherein said first and said second selected scintillator materials are High-Z scintillator materials.

64. The scintillation detector array of claim 55 wherein said first selected scintillator material is Cerium-doped Lutetium Oxyorthosilicate and said second selected scintillator material is Cerium-doped Gadolinium Oxyorthosilicate.

65. The scintillation detector array of claim 55 wherein said first selected scintillator material is composed of Thallium-doped Sodium Iodide and said second selected scintillator material is Cerium-doped Lutetium Oxyorthosilicate.

66. The scintillation detector array of claim 65 wherein said Thallium-doped Sodium Iodide layer is disposed proximate a subject side and said Cerium-doped Lutetium Oxyorthosilicate layer is optically bonded to said non-inverted segmented light guide.

67. The scintillation detector array of claim 65 wherein said Cerium-doped Lutetium Oxyorthosilicate layer is chemically etched to optical transparency with pyrophosphoric acid.

68. The scintillation detector array of claim 65 wherein said Cerium-doped Lutetium Oxyorthosilicate is mechanically polished to optical transparency.

69. The scintillation detector array of claim 66 wherein said first selected scintillator material is Cerium-doped Yttrium Oxyorthosilicate and said second selected scintillation material is Cerium-doped Lutetium Oxyorthosilicate.

70. The scintillation detector array of claim 69 wherein said Cerium-doped Yttrium Oxyorthosilicate layer is disposed proximate a subject side and said Cerium-doped Lutetium Oxyorthosilicate layer is optically bonded to said non-inverted segmented light guide.

71. The scintillation detector array of claim 69 wherein said Cerium-doped Lutetium Oxyorthosilicate layer and said Cerium-doped Yttrium Oxyorthosilicate layer are chemically etched to optical transparency using pyrophosphoric acid.

72. The scintillation detector array of claim 69 wherein said Cerium-doped Lutetium Oxyorthosilicate layer and said Cerium-doped Yttrium Oxyorthosilicate layer are mechanically polished to optical transparency.

* * * * *